United States Patent
Yui et al.

(10) Patent No.: US 12,181,556 B2
(45) Date of Patent: Dec. 31, 2024

(54) MRI APPARATUS

(71) Applicant: CANON MEDICAL SYSTEMS CORPORATION, Otawara (JP)

(72) Inventors: Masao Yui, Otawara (JP); Aina Ikezaki, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 64 days.

(21) Appl. No.: 17/804,220

(22) Filed: May 26, 2022

(65) Prior Publication Data

US 2022/0397626 A1    Dec. 15, 2022

(30) Foreign Application Priority Data

Jun. 11, 2021   (JP) ................................ 2021-098207

(51) Int. Cl.
*G01R 33/561*   (2006.01)
*G01R 33/44*    (2006.01)
(Continued)

(52) U.S. Cl.
CPC ......... *G01R 33/5617* (2013.01); *G01R 33/50* (2013.01); *G01R 33/543* (2013.01);
(Continued)

(58) Field of Classification Search
CPC .. G01R 33/5617; G01R 33/50; G01R 33/543; G01R 33/56341; G01R 33/448; G01R 33/56509; A61B 5/004; A61B 5/055
See application file for complete search history.

(56) References Cited

U.S. PATENT DOCUMENTS

| | | | | |
|---|---|---|---|---|
| 5,560,360 A | * | 10/1996 | Filler ............... | G01R 33/56341 600/408 |
| 2016/0202338 A1 | * | 7/2016 | Kimura ............. | G01R 33/5608 324/309 |

(Continued)

FOREIGN PATENT DOCUMENTS

JP    2017-225501 A    12/2017

OTHER PUBLICATIONS

Oshio et al., "The Spatial Distribution of Water Components with Similar $T_2$ May Provide Insight into Pathways for Large Molecule Transportation in the Brain", Magn Reson Med Sci, 2020, doi:10.2463/mrms.mp.2019-0138, 6 Pages.

(Continued)

*Primary Examiner* — Rishi R Patel
(74) *Attorney, Agent, or Firm* — Oblon, McClelland, Maier & Neustadt, L.L.P.

(57) ABSTRACT

In one embodiment, an MRI apparatus includes: processing circuitry configured to: set a first pulse sequence and a second pulse sequence, wherein, in the first pulse sequence, a first gradient pulse is applied between two adjacent refocusing pulses, and, in the second pulse sequence, a second gradient pulse being different in pulse shape from the first gradient pulse is applied between two adjacent refocusing pulses, wherein: the scanner is configured to acquire first signals and second signals; and the processing circuitry is configured to generate at least one first image and at least one second image; and calculate a T2 value of a body fluid of the object from the at least one first image and the at least one second image in such a manner that influence of movement including diffusion of the body fluid is removed.

18 Claims, 16 Drawing Sheets

(51) Int. Cl.
*G01R 33/50* (2006.01)
*G01R 33/54* (2006.01)
*G01R 33/563* (2006.01)
*G01R 33/565* (2006.01)
*A61B 5/00* (2006.01)
*A61B 5/055* (2006.01)

(52) U.S. Cl.
CPC . *G01R 33/56341* (2013.01); *G01R 33/56509* (2013.01); *A61B 5/004* (2013.01); *A61B 5/055* (2013.01); *G01R 33/448* (2013.01)

(56) References Cited

U.S. PATENT DOCUMENTS

2017/0363699 A1* 12/2017 Ookawa ............... G01R 33/543
2018/0067183 A1* 3/2018 Choi .................. G01R 33/5615

OTHER PUBLICATIONS

Extended European Search Report issued Oct. 25, 2022, in corresponding European Patent Application No. 22175386.6, 8 pages.
Natalie Bnaiahu et al: "The generalized effect of diffusion on quantitative T2 mapping in preclinical scanners" Proceedings of The International Society for Magnetic Resonance in Medicine, 27TH Annual Meeting and Exhibition, vol. 27, 3217, Apr. 26, 2019, XP040710603.
Shepherd Timothy M. et al: "New rapid, accurate $T_2$ quantification detects pathology in normal-appearing brain regions of relapsing-remitting MS patients", Neuroimage: Clinical, vol. 14, Feb. 3, 2017, pp. 363-370, XP055966945.
Umesh Rudrapatna S. et al.: "Measurement of distinctive features of cortical spreading depolarizations with different MRI contrasts", NMR in Biomedicine., vol. 28, No. 5, Mar. 27, 2015, pp. 591-600, XP055966069.

* cited by examiner

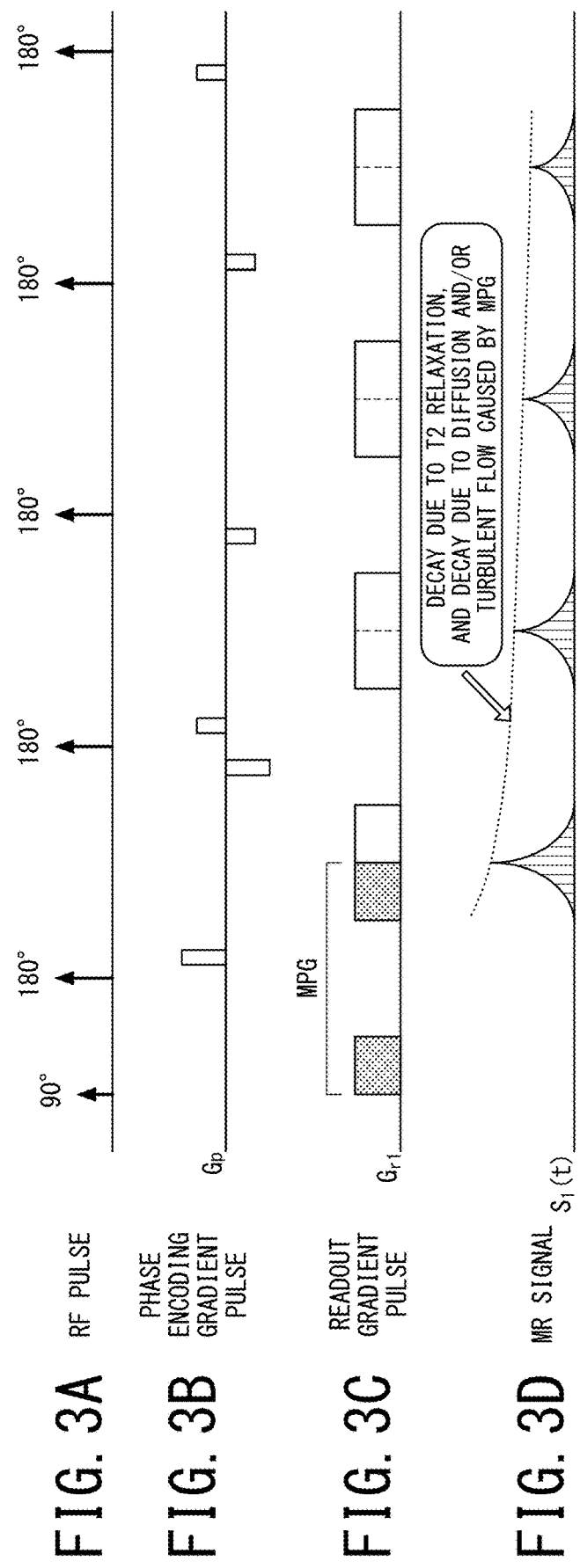

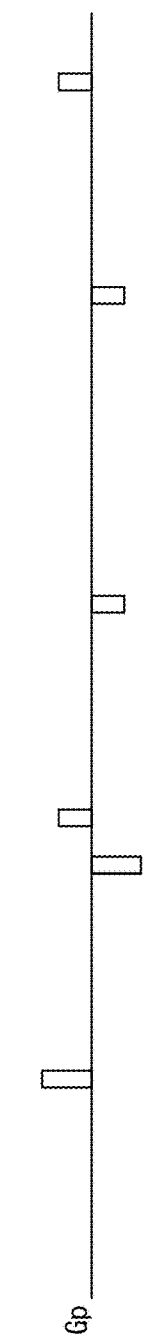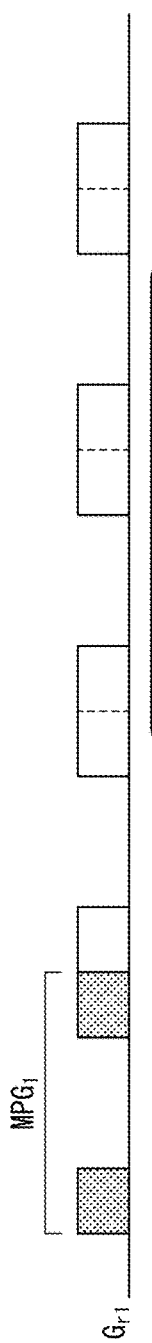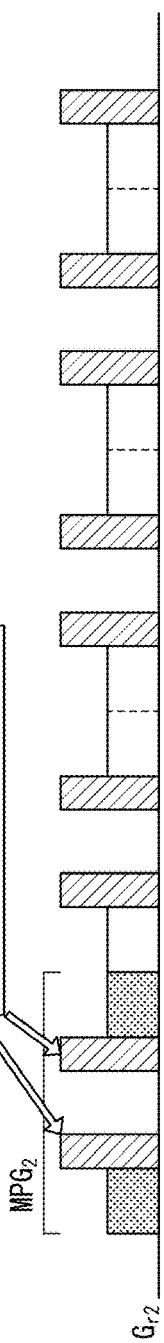
FIG. 4A, FIG. 4B, FIG. 4C, FIG. 4D, FIG. 4E, FIG. 4F

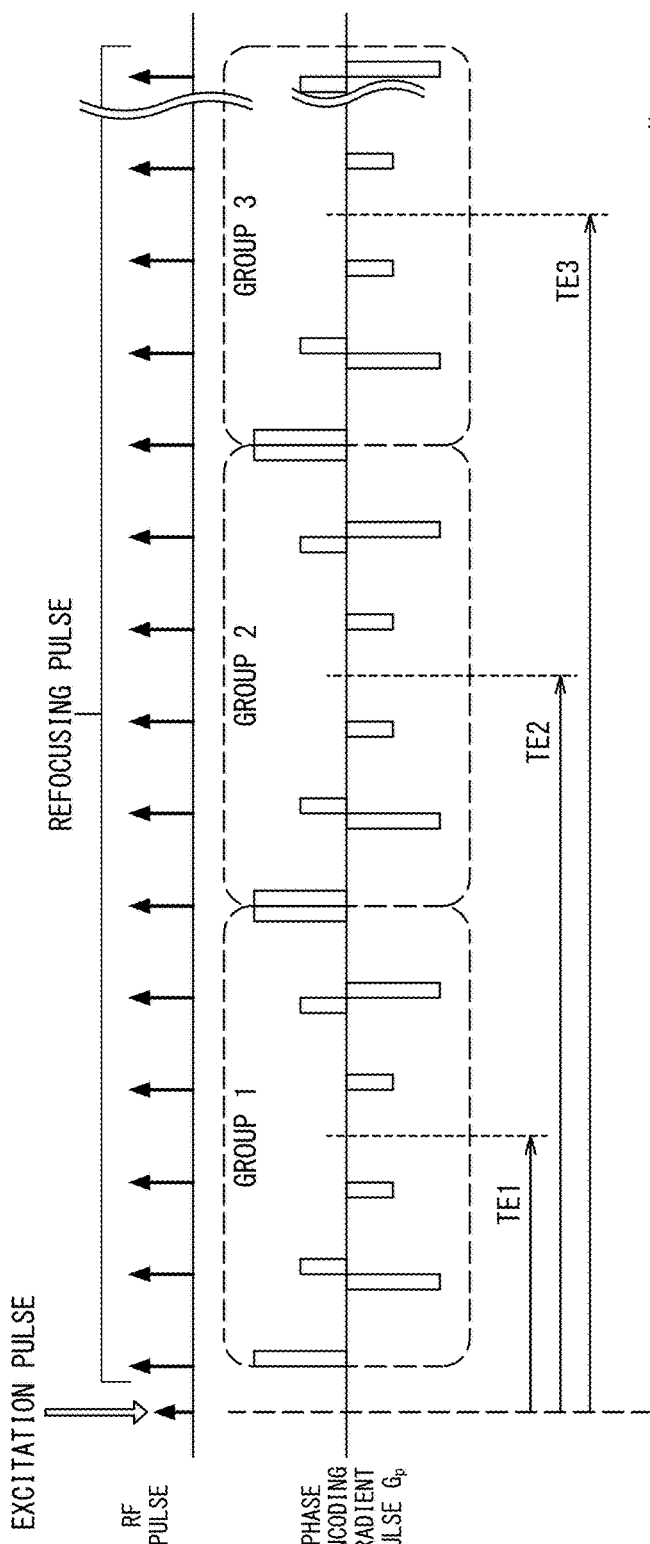

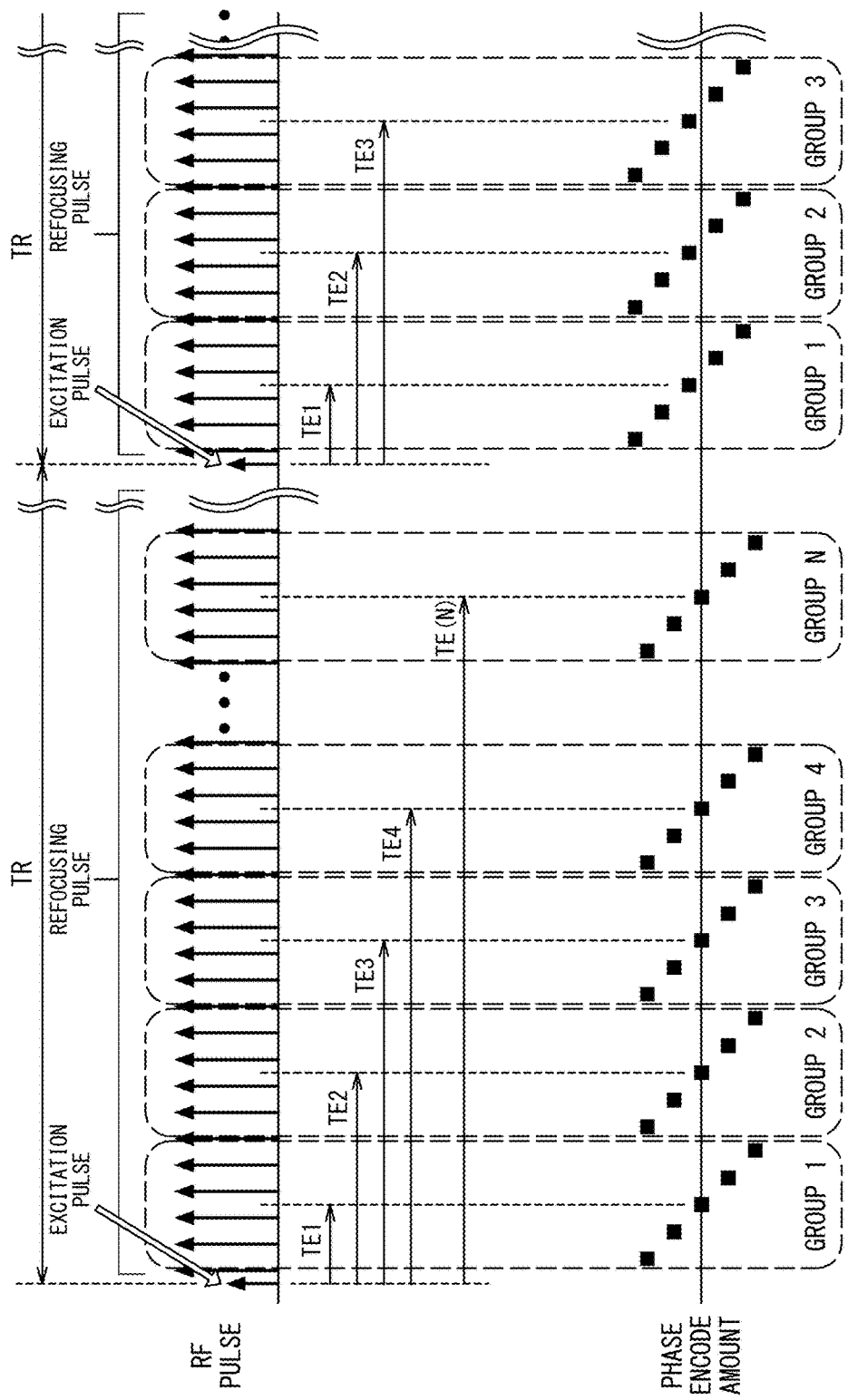

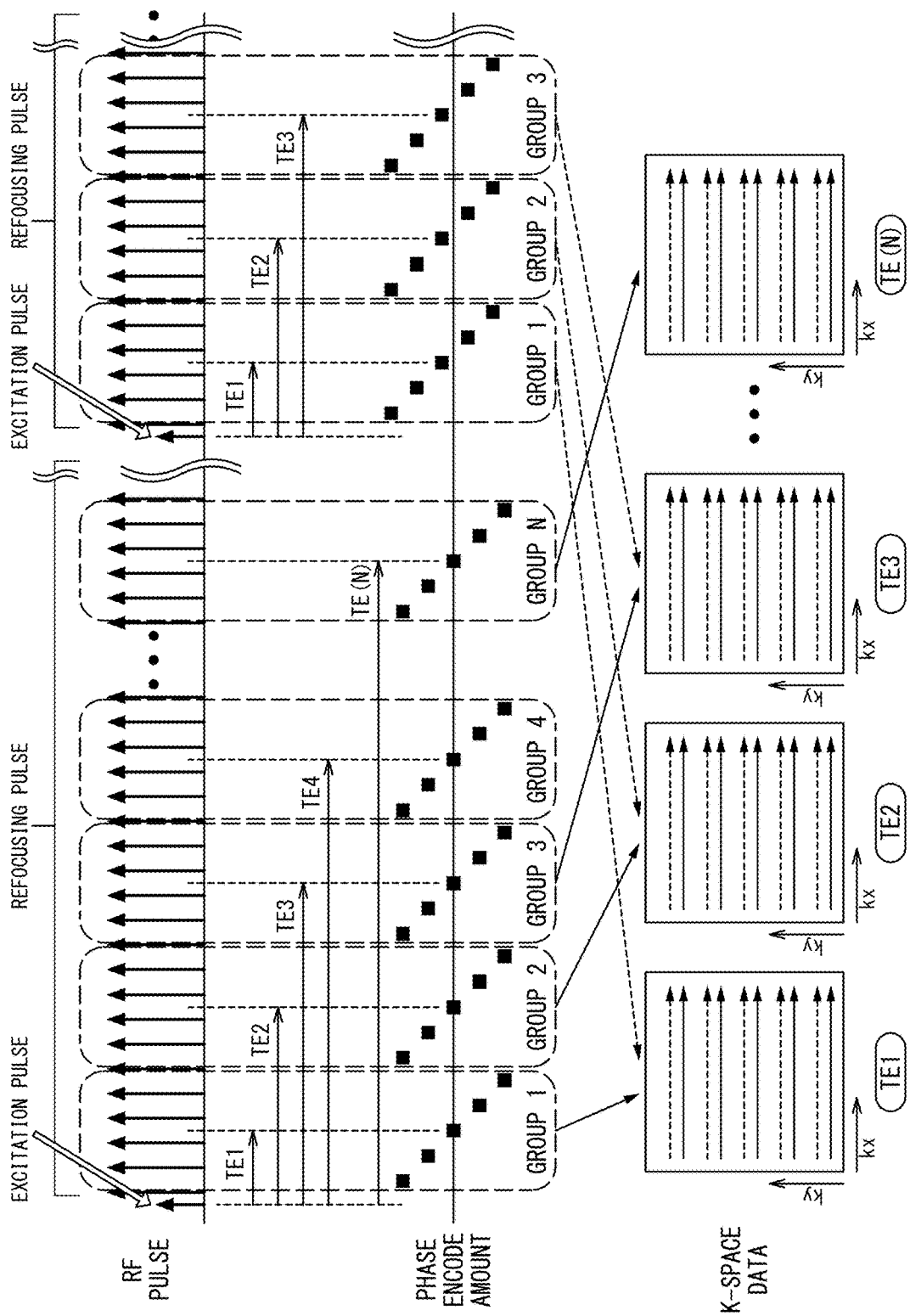

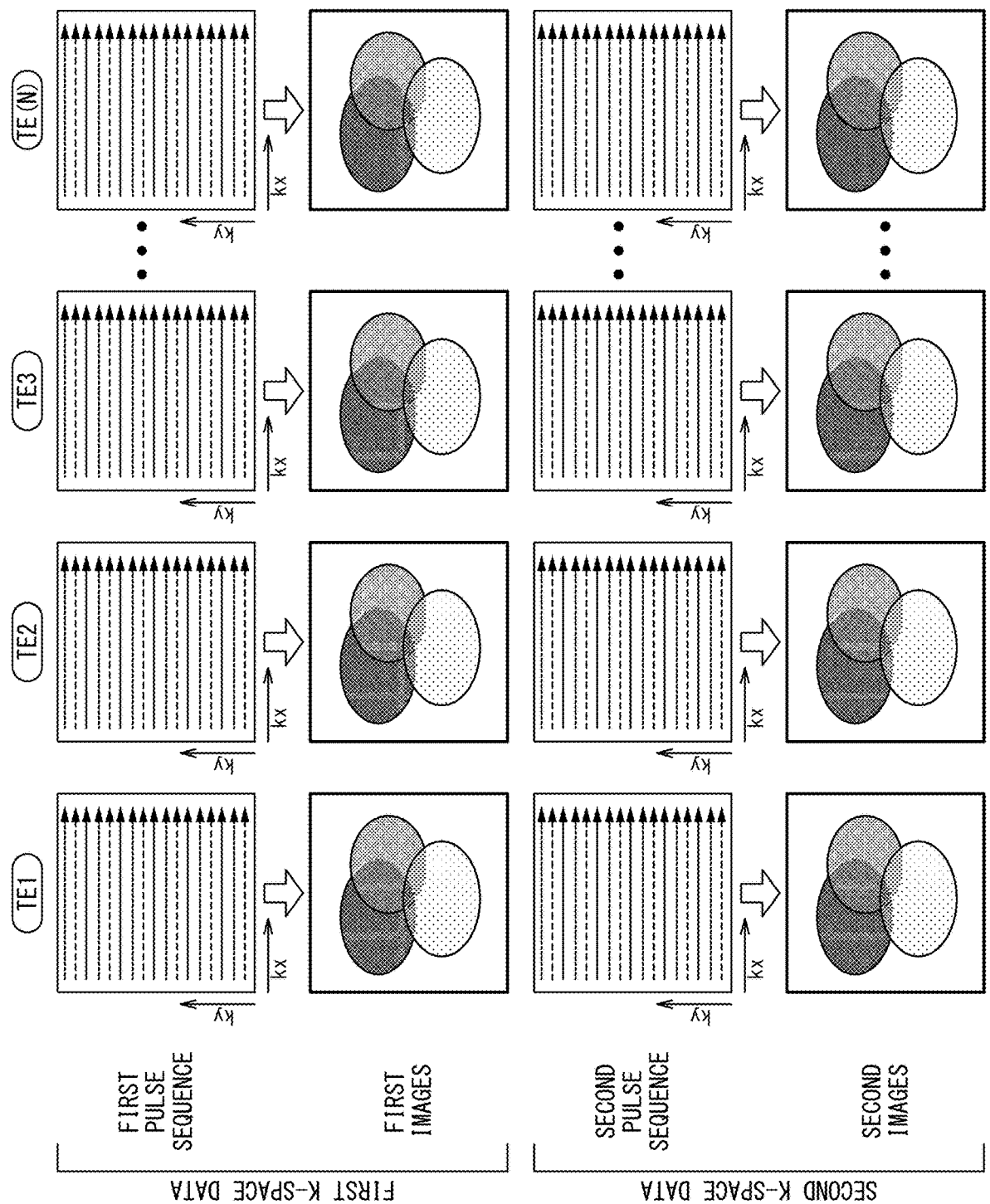

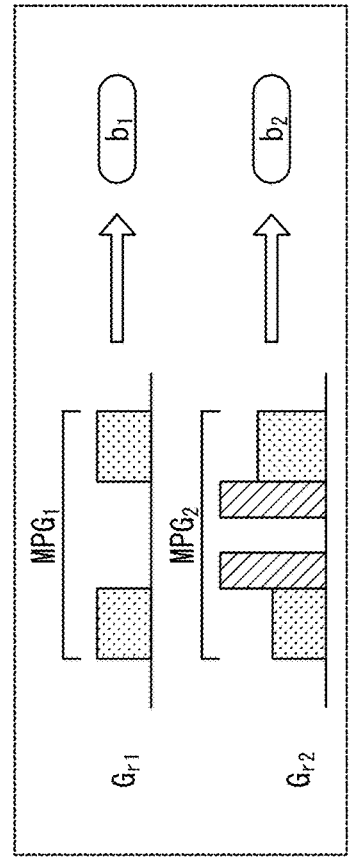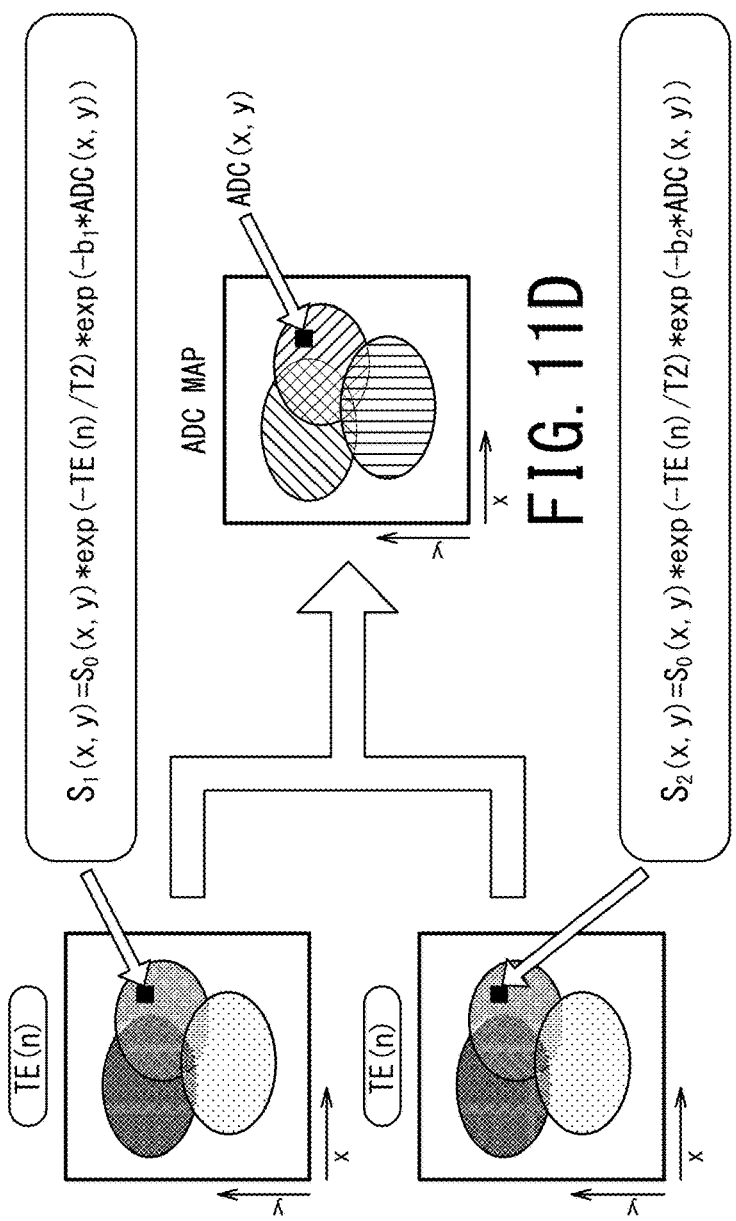

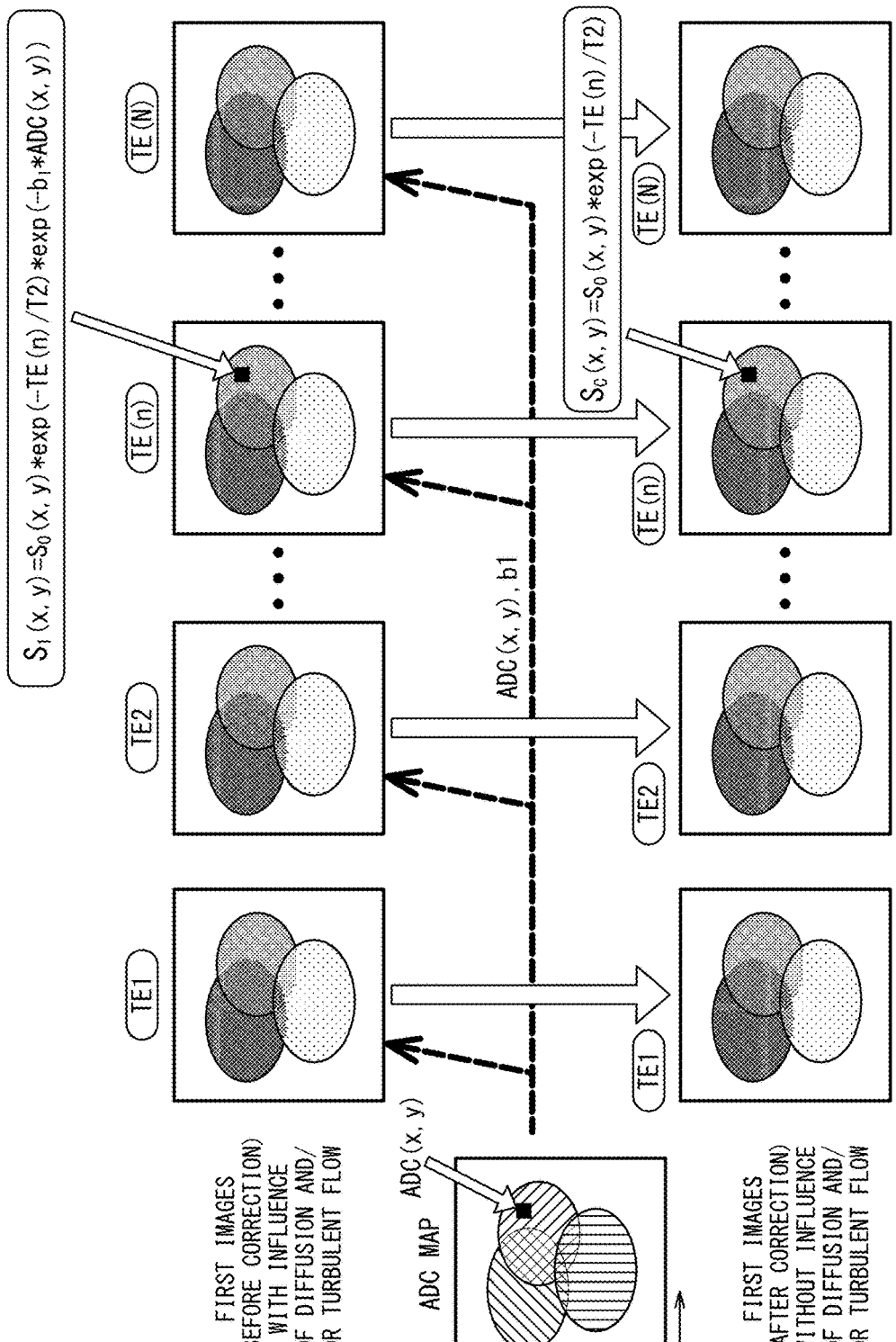
FIG. 12A FIRST IMAGES (BEFORE CORRECTION) WITH INFLUENCE OF DIFFUSION AND/OR TURBULENT FLOW
FIG. 12B ADC MAP
FIG. 12C FIRST IMAGES (AFTER CORRECTION) WITHOUT INFLUENCE OF DIFFUSION AND/OR TURBULENT FLOW

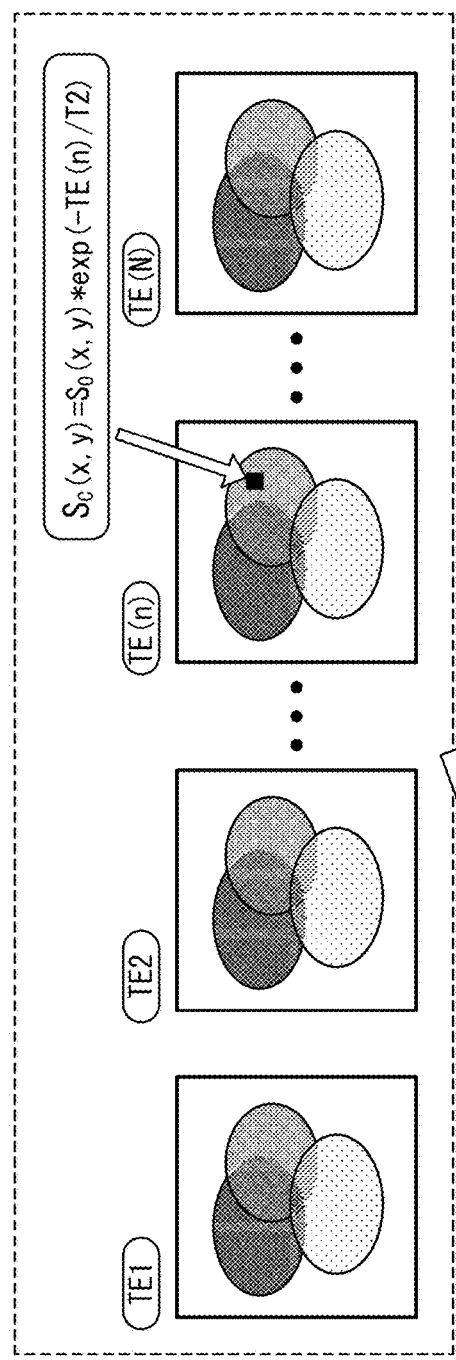
FIG. 13A
FIRST IMAGES
(AFTER CORRECTION)
WITHOUT INFLUENCE OF
DIFFUSION AND/OR
TURBULENT FLOW
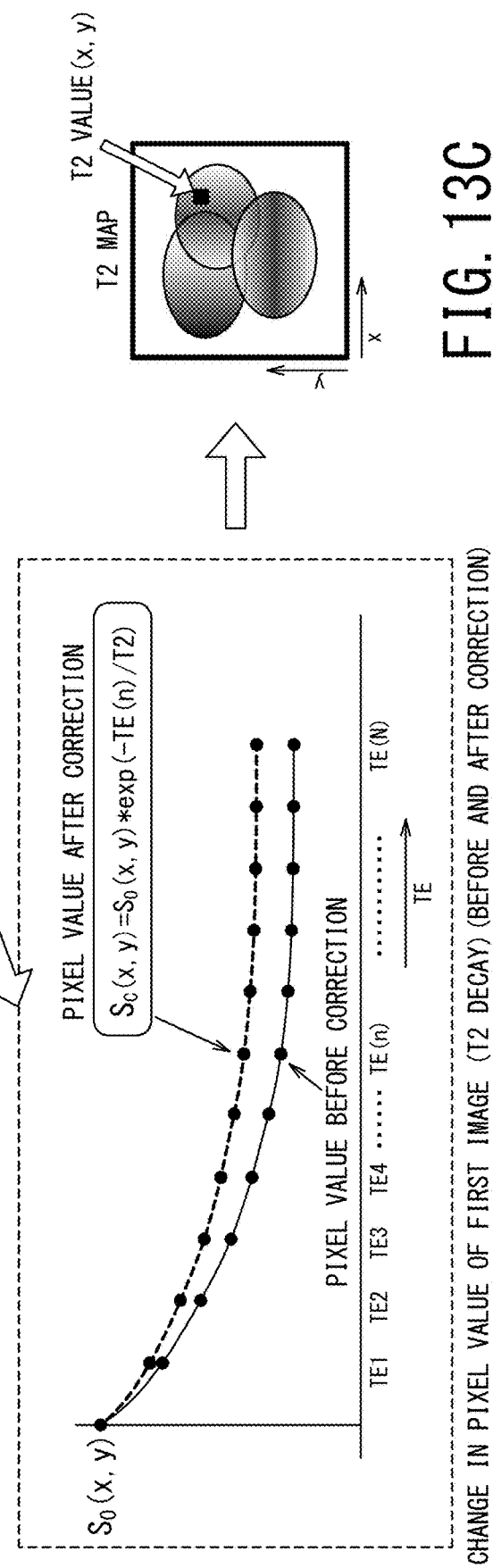
FIG. 13B
FIG. 13C

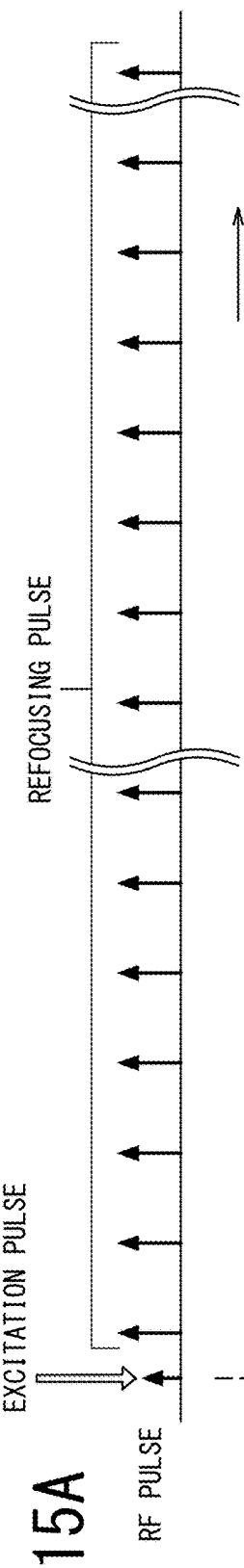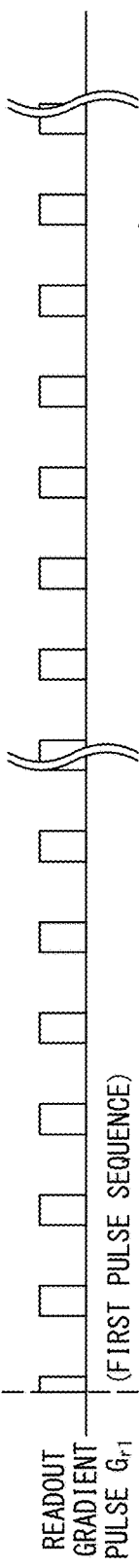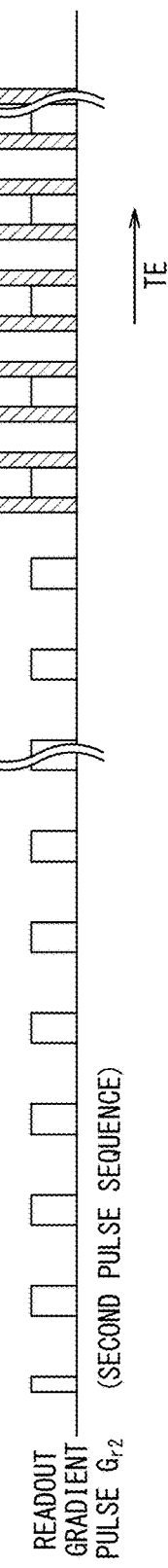

FIRST IMAGES
(AFTER CORRECTION)
INFLUENCE OF DIFFUSION
AND/OR TURBULENT
FLOW IS REMOVED

CHANGE IN PIXEL VALUE OF FIRST IMAGE (T2 DECAY) (BEFORE AND AFTER CORRECTION)

MRI APPARATUS

CROSS-REFERENCE TO RELATED APPLICATIONS

This application claims the benefit of priority of Japanese Patent Application No. 2021-098207, filed Jun. 11, 2021, the entire contents of which are incorporated herein by reference.

FIELD

Disclosed Embodiments relate to a magnetic resonance imaging (MRI) apparatus.

BACKGROUND

An MRI apparatus is an imaging apparatus which excites nuclear spin of an object placed in a static magnetic field with a radio frequency (RF) pulse having the Larmor frequency, and reconstructs an image based on the magnetic resonance (MR) signals emitted from the object due to the excitation.

The MRI apparatus can image cerebrospinal fluid (CSF) and cerebral interstitial fluid, for example. In recent years, cerebrospinal fluid and cerebral interstitial fluid are called neurofluid and are considered to be important in elucidating the clearance function of removing waste products from the brain. Images of neurofluid are exemplified by a T2-weighted image and a diffusion-weighted image.

In order to properly depict neurofluid such as CSF in a T2-weighted image, it is necessary to separate the parenchyma of the brain, and a pulse sequence called a CPMG (Carr-Purcell-Meiboom-Gill) sequence or a FSE (Fast Spin Echo) sequence is often used. Meanwhile, in diffusion-weighted images, attempts have been made to image not only diffusion by Brownian motion but also perfusion and/or movement by turbulent flow.

Regions of interest for imaging neurofluid are, for example, perivascular space in the brain (i.e., gap around blood vessels in the brain), narrow cerebral sulcus (i.e., wrinkled grooves in the brain), and a brain surface. Thus, imaging methods for such narrow regions require high spatial resolution.

In order to acquire a T2-weighted image or T2 mapping with high resolution using the CPMG (or FSE) sequence described above, it is necessary to increase the strength G and pulse length $T_s$ of the readout gradient pulse.

However, by increasing the strength G and pulse length $T_s$ of readout gradient pulse, the influence of diffusion and/or turbulent flow due to the readout gradient pulse itself cannot be ignored, which may deteriorate the accuracy of the T2 value in T2 mapping.

It should be noted that, in the assessment related to the clearance of waste products from the brain, the T2 value of neurofluid, which is not influenced by diffusion and/or turbulent flow, is important, while an index related to diffusion and/or turbulent flow of neurofluid is also important.

As described above, in the conventional imaging method, the accuracy of the T2 value in T2 mapping is reduced due to the influence of diffusion and/or turbulent flow of neurofluid. In addition, in order to obtain an index related to diffusion and/or turbulent flow, it is required to perform an imaging sequence other than an imaging sequence for acquiring the T2 value, and the overall imaging time becomes longer (for example, JP 2017-225501 A).

BRIEF DESCRIPTION OF THE DRAWINGS

In the accompanying drawings:

FIG. 3A to FIG. 3D are sequence diagrams illustrating conventional problems in CSF imaging;

FIG. 4A to FIG. 4F are overall sequence diagrams of the first and second pulse sequences of the present embodiment;

FIG. 7A and FIG. 7B are respectively sequence diagrams of the RF pulse and the phase encoding gradient pulse GP that are common to the first and second pulse sequences;

FIG. 7C is a sequence diagram of the readout gradient pulse of the first pulse sequence;

FIG. 7D is a sequence diagram of the readout gradient pulse of the second pulse sequence;

FIG. 8A and FIG. 8B are sequence diagrams of the first and second pulse sequences when viewed over a longer time span than those in FIG. 7A to FIG. 7D;

FIG. 9A to FIG. 9C are schematic diagrams illustrating a concept of filling a k-space with k-space data acquired in a plurality of segments;

FIG. 10A and FIG. 10B are schematic diagrams illustrating the concept of generating a first image for each echo time by reconstructing a first k-space dataset for each echo time;

FIG. 10O and FIG. 10D are schematic diagrams illustrating a concept of generating a second image for each echo time by reconstructing a second k-space dataset for each echo time;

FIG. 11A to FIG. 11D are schematic diagrams illustrating a processing concept of calculating an ADC map from respective pixel values of the first and second images and the first and second b-values;

FIG. 12A to FIG. 12C are schematic diagrams illustrating a processing concept of correcting the first image generated for each echo time and removing the influence of diffusion and/or turbulent flow by using the ADC map;

FIG. 13A to FIG. 13C are schematic diagrams illustrating a processing concept of generating a T2 map by calculating a true T2 value, from which influence of diffusion and/or turbulent flow is removed, for each pixel position from change in pixel value of the first image after correction with respect to the echo time TE;

FIG. 15A to FIG. 15C are sequence diagrams of the first and second pulse sequences according to the first modification of the present embodiment.

DETAILED DESCRIPTION

Hereinbelow, embodiments of an MRI apparatus 1 according to the present invention will be described by referring to the accompanying drawings.

In one embodiment, an MRI apparatus according to one embodiment includes: a scanner that includes a static magnetic field magnet, a gradient coil, a whole body coil, and an RF transmitter; and processing circuitry configured to: set a first pulse sequence and a second pulse sequence, each of which is a fast spin echo (FSE) pulse sequence in which a plurality of refocusing pulses are applied subsequent to an application of an excitation pulse, wherein, in the first pulse sequence, a first gradient pulse is applied between two adjacent refocusing pulses, and, in the second pulse sequence, a second gradient pulse being different in pulse shape from the first gradient pulse is applied between two adjacent refocusing pulses, wherein: the scanner is configured to apply the first pulse sequence and the second pulse sequence to an object and acquire first signals in the first pulse sequence and second signals in the second pulse sequence; and the processing circuitry is configured to generate at least one first image from the first signals and at least one second image from the second signals; and calculate a T2 value of a body fluid of the object from the at least one first image and the at least one second image in a manner that influence of movement including diffusion of the body fluid is removed from the T2 value.

Configuration and Basic Operation

Figure 1:
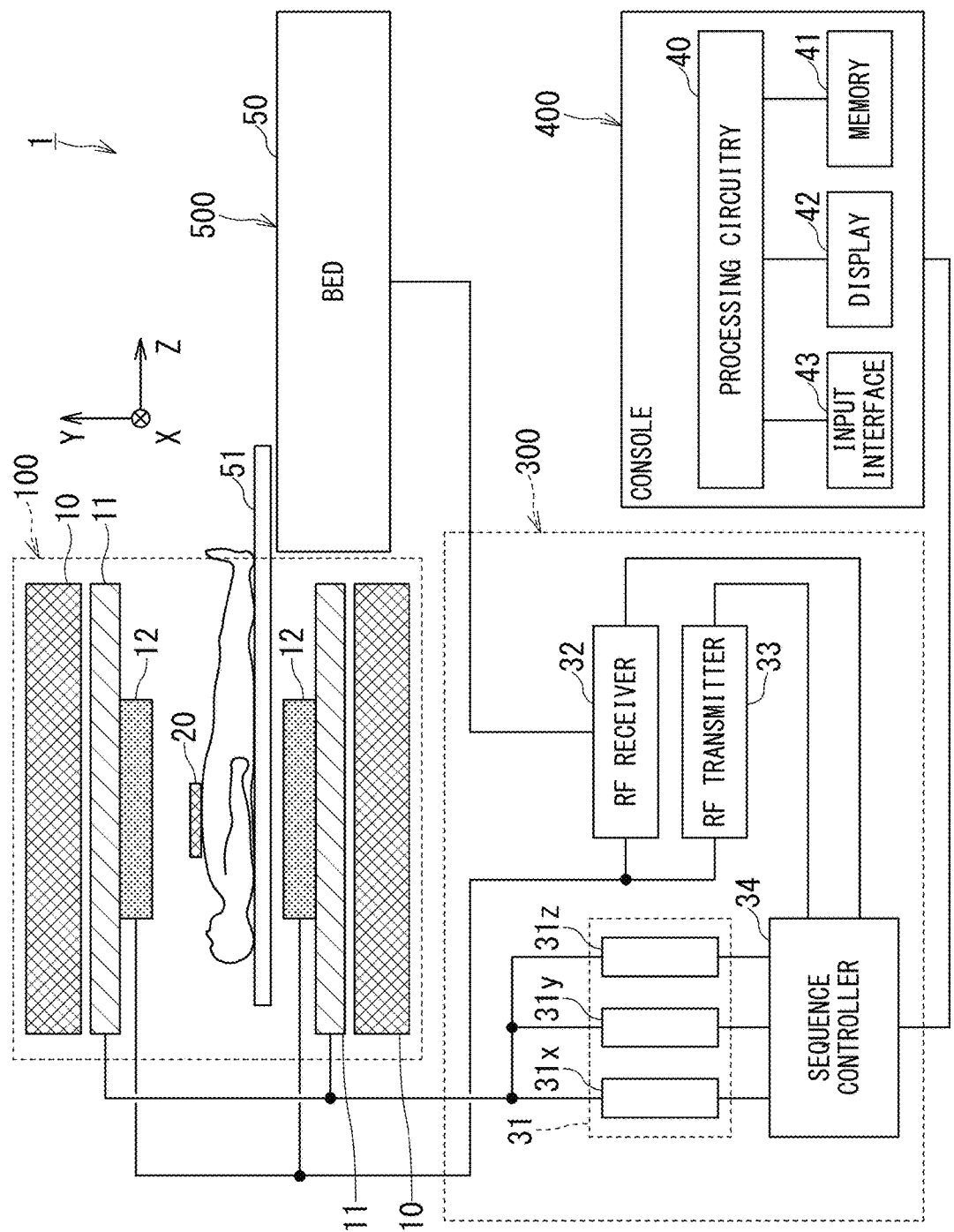
FIG. 1 is a configuration diagram illustrating an overall configuration of an MRI apparatus according to the present embodiment.

FIG. 1 is a block diagram illustrating the overall configuration of the MRI apparatus 1 of the present embodiment. The MRI apparatus 1 of the present embodiment includes components such as a gantry 100, a control cabinet 300, a console 400, and a bed 500.

The gantry 100 includes, for example, a static magnetic field magnet 10, a gradient coil 11, a WB (whole body) coil 12, and these components are included in a cylindrical housing. The bed 500 includes a bed body 50 and a table 51. Additionally, the MRI apparatus 1 further includes an array coil 20 that is provided near an object.

The control cabinet 300 includes three gradient coil power supplies 31 (to be exact, 31$x$ for the X-axis, 31$y$ for the Y-axis, and 31$z$ for the Z-axis), an RF receiver 32, an RF transmitter 33, and a sequence controller 34.

The static magnetic field magnet 10 of the gantry 100 is substantially in the form of a cylinder, and generates a static magnetic field inside the bore (i.e., the space inside the cylindrical structure of the static magnetic field magnet 10), which is an imaging region of an object (for example, a patient). The static magnetic field magnet 10 includes a superconducting coil inside, and the superconducting coil is cooled down to an extremely low temperature by liquid helium. The static magnetic field magnet 10 generates a static magnetic field by supplying the superconducting coil with electric current provided from a static magnetic field power supply (not shown) in an excitation mode. Afterward, the static magnetic field magnet 10 shifts to a permanent current mode, and the static magnetic field power supply is separated. Once it enters the permanent current mode, the static magnetic field magnet 10 continues to generate a strong static magnetic field for a long time, for example, over one year. Note that the static magnetic field magnet 10 may be configured as a permanent magnet.

The gradient coil 11 is also substantially in the form of a cylinder, and is fixed to the inside of the static magnetic field magnet 10. This gradient coil 11 applies gradient magnetic fields to an object in the respective directions of the X-axis, the Y-axis, and the Z-axis of the apparatus shown in FIG. 1, by using electric currents supplied from the gradient coil power supplies 31$x$, 31$y$, and 31$z$.

The bed body 50 of the bed 500 can move the table 51 in the upward and downward directions, and moves the table 51 with the object loaded thereon to a predetermined height before imaging. Afterward, at the time of imaging, the bed body 50 moves the table 51 in the horizontal direction so as to move the object to the inside of the bore.

The WB body coil 12 is shaped substantially in the form of a cylinder so as to surround an object, and is fixed to the inside of the gradient coil 11. The WB coil 12 applies RF pulses transmitted from the RF transmitter 33 to the object, and receives MR signals emitted from the object due to excitation of hydrogen nuclei.

The array coil 20 is an RF coil, and receives the MR signals emitted from the object at positions close to the object. The array coil 20 is, for example, configured of a plurality of coil elements. Although there are various types of array coil 20 such as a head coil, a chest coil, a spine coil, a lower-limb coil, and a whole-body coil for imaging different parts of the object, a chest coil is illustrated as the array coil 20 in FIG. 1.

The RF transmitter 33 transmits RF pulses to the WB coil 12 on the basis of commands inputted from the sequence controller 34. The RF receiver 32 receives MR signals received by the WB coil 12 and/or the array coil 20, and transmits raw data obtained by digitizing the received MR signals to the sequence controller 34.

The sequence controller 34 performs a scan of the object by driving the gradient coil power supplies 31, the RF transmitter 33, and the RF receiver 32 under the control of the console 400. By performing such scan, the sequence controller 34 receives the raw data from the RF receiver 32 and transmits the received raw data to the console 400.

The sequence controller 34 includes processing circuitry (not shown), which is configured as hardware such as a processor for executing predetermined programs, a field programmable gate array (FPGA), and an application specific integrated circuit (ASIC).

The console 400 is configured as a computer including processing circuitry 40, a memory 41, a display 42, and an input interface 43.

The memory 41 is a recording medium including a read-only memory (ROM) and a random access memory (RAM) in addition to an external memory device such as a hard disk drive (HDD) and an optical disc device. The memory 41 stores various data and information as well as various programs to be executed by a processor of the processing circuitry 40.

The input interface 43 includes various devices for an operator to input various data and information, and is configured of, for example, a mouse, a keyboard, a trackball, and/or a touch panel.

The display 42 is a display device such as a liquid crystal display panel, a plasma display panel, and an organic EL panel.

The processing circuitry 40 is, for example, a circuit provided with a CPU and/or a special-purpose or general-purpose processor. The processor implements various functions described below by executing programs stored in the memory 41. The processing circuitry 40 may be configured of hardware such as an FPGA and an ASIC. The various functions described below can also be implemented by such hardware. Additionally, the processing circuitry 40 can implement the various functions by combining hardware processing and software processing based on its processor and programs.

The console 400 performs entire system control of the MRI apparatus 1 with these components. Specifically, the console 400 receives various commands and information such as imaging conditions, which are inputted by an operator (e.g., a medical imaging technologist) through the mouse and/or the keyboard of the input interface 43. The processing circuitry 40 causes the sequence controller 34 to perform a scan based on the inputted imaging conditions, and reconstructs images using the raw data transmitted from the sequence controller 34. The reconstructed images are displayed on the display 42 and stored in the memory 41.

Detailed Configuration and Operation

Figure 2:
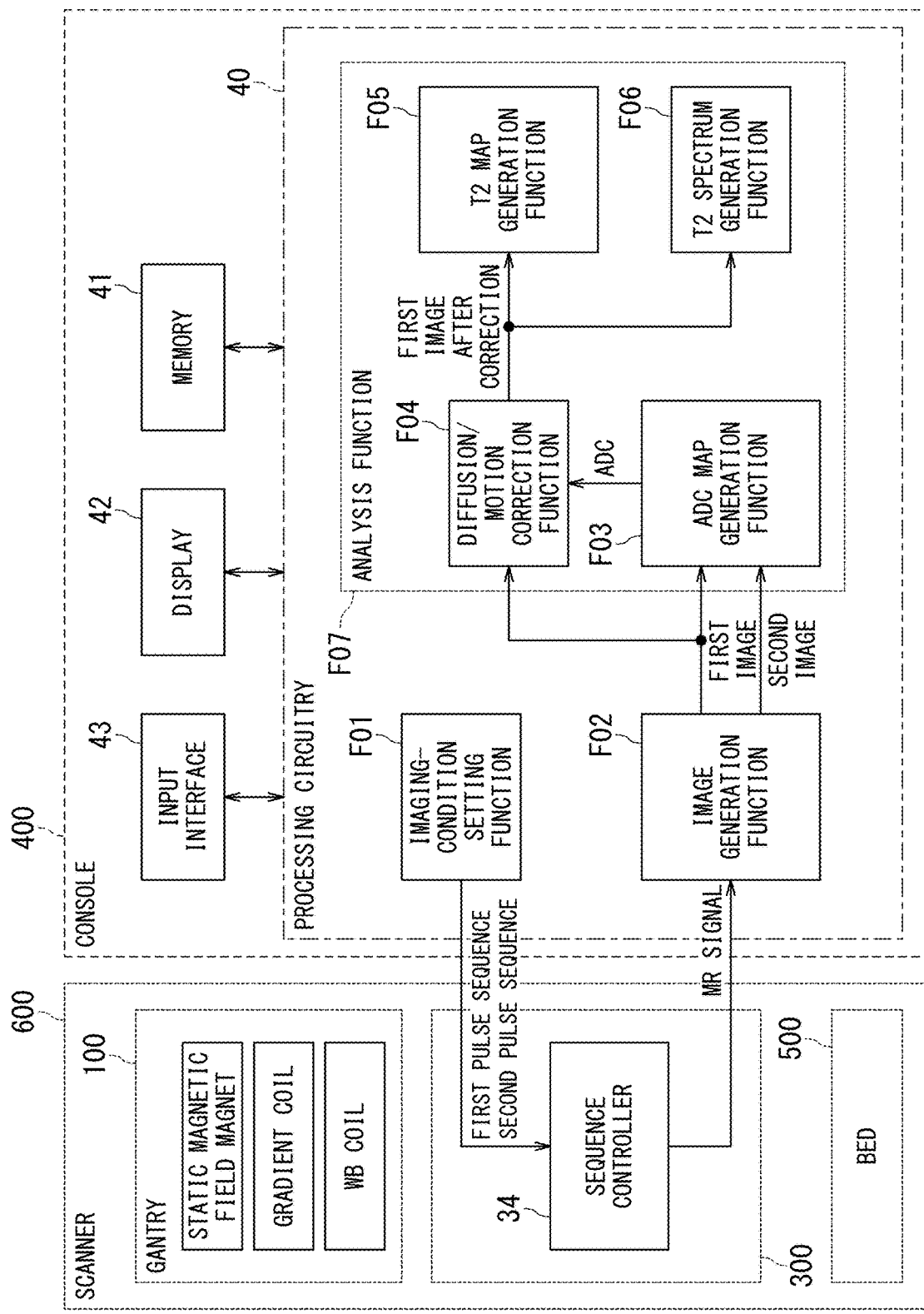
FIG. 2 is a functional block diagram focusing on the functions to be implemented by the processing circuitry of the present embodiment.

FIG. 2 is a block diagram of the MRI apparatus 1 of the present embodiment, and a functional block diagram particularly focusing on the functions achieved by the processing circuitry 40.

Of the components of the MRI apparatus 1 shown in FIG. 1, the components excluding the console 400 (i.e., the entirety of the gantry 100, the control cabinet 300, and the bed 500) constitute a scanner 600, as illustrated in FIG. 2.

As shown in FIG. 2, the processing circuitry 40 of the MRI apparatus 1 implements each of an imaging-condition setting function F01, an image generation function F02, an ADC map generation function F03, a diffusion/motion correction function F04, a T2 map generation function F05, and a T2 spectrum generation function F06. Note that the ADC map generation function F03, the diffusion/motion correction function F04, the T2 map generation function F05, and the T2 spectrum generation function F06 are collectively referred to as an analysis function F07.

The imaging-condition setting function F01 determines parameters of the pulse sequence based on the imaging conditions selected or set via, for example, the input interface 43, and sets the pulse sequence having the determined parameters on the sequence controller 34 of the scanner 600.

In particular, the MRI apparatus 1 of the present embodiment can set a first and second pulse sequences of FSE (Fast Spin Echo). In the first pulse sequence, an excitation pulse is applied, and a plurality of refocusing pulses are applied subsequent to this excitation pulse such that a first gradient pulse is also applied between any two adjacent refocusing pulses (i.e., between one refocusing pulse and the next refocusing pulse or between two refocusing pulses closest to each other). In the second pulse sequence, a second gradient pulse having different pulse shape from the first gradient pulse is applied between any two adjacent refocusing pulses. The first and second pulse sequences will be described below in more detail.

The scanner 600 applies the first and second pulse sequences to the object to acquire the first and second MR signals, and sends the first second MR signals to the processing circuitry 40 of the console 400 via the sequence controller 34.

The image generation function F02 of the processing circuitry 40 generates a first image from the first MR signals and generates a second image from the second MR signals. For example, the image generation function F02 reconstructs the first MR signals and the second MR signals by processing such as Fourier transform to generate the first and second images.

The analysis function F07 uses the first image and the second image to calculate the T2 value of the body fluid. The T2 value herewith refers to a value from which the influence of the movement including the diffusion of the body fluid of the object is removed.

Note that the body fluid of the object is, for example, neurofluid such as CSF (cerebrospinal fluid) or cerebral interstitial fluid. Further, the body fluid of the object may include blood, lymph, or other fluid inside the object.

Prior to detailed description of the ADC map generation function F03, the diffusion/motion correction function F04, the T2 map generation function F05, and the T2 spectrum generation function F06, a description will be given of the conventional problems in imaging neurofluid such as CSF, and the means for solving the conventional problems according to the present embodiment, by referring to FIG. 3A to FIG. 5. Although the target of the imaging is assumed to be CSF in the following for the sake of simplifying the description, neurofluid such as cerebral interstitial fluid and other body fluid are not excluded from the target of the imaging.

FIG. 3A to FIG. 3D are sequence diagrams showing the conventional problems in CSF imaging. Since body fluids such as CSF have a longer transverse relaxation time T2 than the parenchyma of the brain, T2-weighted images are often used as images of CSF. In particular, in order to obtain a well depicted image of the CSF, it is necessary to sufficiently separate the parenchyma of the brain, thereby a pulse sequence called a Carr-Purcell-Meiboom-Gill (CPMG) sequence or a Fast Spin Echo (FSE) sequence has been often used conventionally.

The CPMG sequence is an FSE pulse sequence that satisfies the so-called CPMG conditions. The CPMG sequence needs to satisfy both of the following two conditions (1) and (2).

CPMG condition (1): The interval between any two adjacent refocusing pulses (i.e., ESP: echo spacing) is twice the interval between the excitation pulse and the first refocusing pulse, and the phase of the refocusing pulse is shifted by 90° from the phase of the excitation pulse.

CPMG condition (2): Among all two adjacent refocusing pulses, the integral value of all the gradient magnetic fields between the two adjacent refocusing pulses are the same.

When the CPMG conditions are satisfied, the spin echo SE and the stimulated echo STE are added in the same phase at the same position in the time axis, and thus, the signal to noise ratio (SNR) is improved.

FIG. 3A to FIG. 3C illustrate CPMG sequences that are conventionally used. FIG. 3A shows an RF pulse train, FIG. 3B shows a phase encoding gradient pulse train, and FIG. 3C shows a readout gradient pulse train. Although a slice selection gradient pulse is also applied at a timing corresponding to the application timing of each RF pulse, it is omitted in FIG. 3A to FIG. 3D.

The application directions of the readout gradient pulse, the phase encoding gradient pulse, and the slice selection gradient pulse are respectively the X-axis direction, the Y-axis direction, and the Z-axis direction in FIG. 1, for example. However, it is not limited to the above-described case but may be desired application directions depending on the inclination of the selected FOV (Field Of View).

As shown in FIG. 3A, the RF pulse train is composed of an excitation pulse (for example, an RF pulse with a flip angle of 90°) and a plurality of refocusing pulses following the excitation pulse (for example, RF pulses with a flip angle of 180°). The excitation pulse and the plurality of refocusing pulses satisfy the above-described CPMG condition (1).

As to the phase encoding gradient pulse GP shown in FIG. 3B, in each interval between two adjacent refocusing pulses, a pair of a phase encoding pulse for determining the phase encode amount and a rewinder pulse are applied. The rewinder pulse has the same amplitude as the phase encoding pulse and has the polarity opposite to that of the phase encoding pulse. With this pair, the CPMG condition (2) described above can be satisfied while setting a different phase encoding amount for each refocusing pulse.

Among the readout gradient pulses $G_{r1}$ shown in FIG. 3C, the gradient pulse between the excitation pulse and the first refocusing pulse is a gradient pulse, so-called pre-phasing pulse, for previously rotating the phase of the transverse magnetization in the negative direction such that the phase of the transverse magnetization becomes zero in the middle of the readout gradient pulse between the first and second refocusing pulses. Usually, the strength of the pre-phasing pulse is set to be the same as the readout gradient pulse, and the pulse length of the pre-phasing pulse is set to be half of the readout gradient pulse.

As described above, in order to acquire a T2-weighted image or T2 mapping for CSF with high resolution, it is necessary to increase at least one of amplitude (i.e., strength) and pulse length of the readout gradient pulse, and correspondingly, the amplitude and/or pulse length of the pre-phasing pulse also increase.

When the amplitude and/or pulse length of each of the pre-phasing pulse and the readout gradient pulse increase, signal decay (i.e., signal attenuation) of each MR signal due to dephasing caused by the diffusion and/or turbulent flow of CSF becomes unignorable.

In other words, the pair of the pre-phasing pulse and the half of the first readout gradient pulse shown as hatched regions in FIG. 3C work in the same way as the MPG (Motion Probing Gradient) pulse in diffusion-weighted imaging, and show the same effect as the MPG pulse. In the following description, such effect is referred to as the MPG effect of the readout gradient pulse. That is, an effect that the signal strength is decayed due to dephasing because of diffusion and/or turbulent flow of CSF caused by application of a readout gradient pulse having large amplitude and/or long pulse length.

FIG. 3D shows each MR signal emitted from the object when the readout gradient pulse is applied. The MR signal peaks at the center of each readout gradient pulse between two adjacent refocusing pulses.

Each peak value of the MR signals is decayed by T2 relaxation along with elapse of time from application of the excitation pulse, as shown by the dotted curve line in FIG. 3D. Conventionally, the transverse relaxation time T2 is calculated from the shape of this decay curve.

However, as described above, when amplitude and/or pulse length of the readout gradient pulse increase, the decay due to the MPG effect is superimposed on the decay due to T2 relaxation. Thus, even if the transverse relaxation time T2 is calculated from the shape of the obtained decay curve, it does not become a true T2 value, but a T2 value with an error. In FIG. 3A to FIG. 3D, the slice selection or slice encoding gradient pulse is omitted.

In some cases, a gradient pulse for suppressing FID signals (i.e., so-called spoiler or crusher gradient pulse) is applied before and after the refocusing pulse, which may also have the MPG effect. In such cases, the MPG effect by the readout gradient pulse is similarly caused as what is shown in FIG. 3D, and the correction method described below can be applied in the same manner.

In order to solve the above-described problem, in the MRI apparatus 1 of the present embodiment, the second pulse sequence is used in addition to the conventional pulse sequence (first pulse sequence) shown in FIG. 3A to FIG. 3D.

FIG. 4A to FIG. 4F illustrate the first and second pulse sequences used in the present embodiment. FIG. 4A to FIG. 4D are the same as the conventional pulse sequence shown in FIG. 3A to FIG. 3D. The pair composed of the pre-phasing pulse and the first half of the readout gradient pulse shown by hatching in FIG. 4C constitute the $MPG_1$ pulse that produces the above-described MPG effect.

The second pulse sequence is the same as the first pulse sequence in terms of RF pulse (FIG. 4A), slice selection gradient pulse (not shown), and phase encoding gradient pulse (FIG. 4B), and is different from the first pulse sequence in terms of readout gradient pulse.

FIG. 4E illustrates the readout gradient pulses $G_{r2}$ in the second pulse sequence. The readout gradient pulse $G_{r2}$ in the second pulse sequence is configured by adding an additional gradient pulse having a predetermined shape (for example, a rectangular shape) to both the front edge and the trailing edge of the readout gradient pulse $G_{r1}$ in the first pulse sequence. Meanwhile, the pre-phasing pulse in the second pulse sequence is configured by adding an additional gradient pulse having the same shape as mentioned above to the trailing edge of the pre-phasing pulse in the first pulse sequence. In FIG. 4E, the pair composed of the pre-phasing pulse shown by hatching and the first half of the readout gradient pulse constitutes an $MPG_2$ pulse that produces the MPG effect in the second pulse sequence.

FIG. 4F shows MR signals emitted from the object when the readout gradient pulse in the second pulse sequence is applied. Each peak value of the MR signals is decayed by T2 relaxation along with elapse of time from the application of the excitation pulse similarly to the first pulse sequence.

As is clear from FIG. 4C and FIG. 4E, the time integral value of the $MPG_2$ pulse in the second pulse sequence is larger than the time integral value of the $MPG_1$ pulse in the first pulse sequence. Thus, the second pulse sequence is larger in MPG effect than the first pulse sequence, and the degree of decay of the peak value of the MR signal due to the elapse of time from the application of the excitation pulse is larger in the second pulse sequence.

Figure 5:
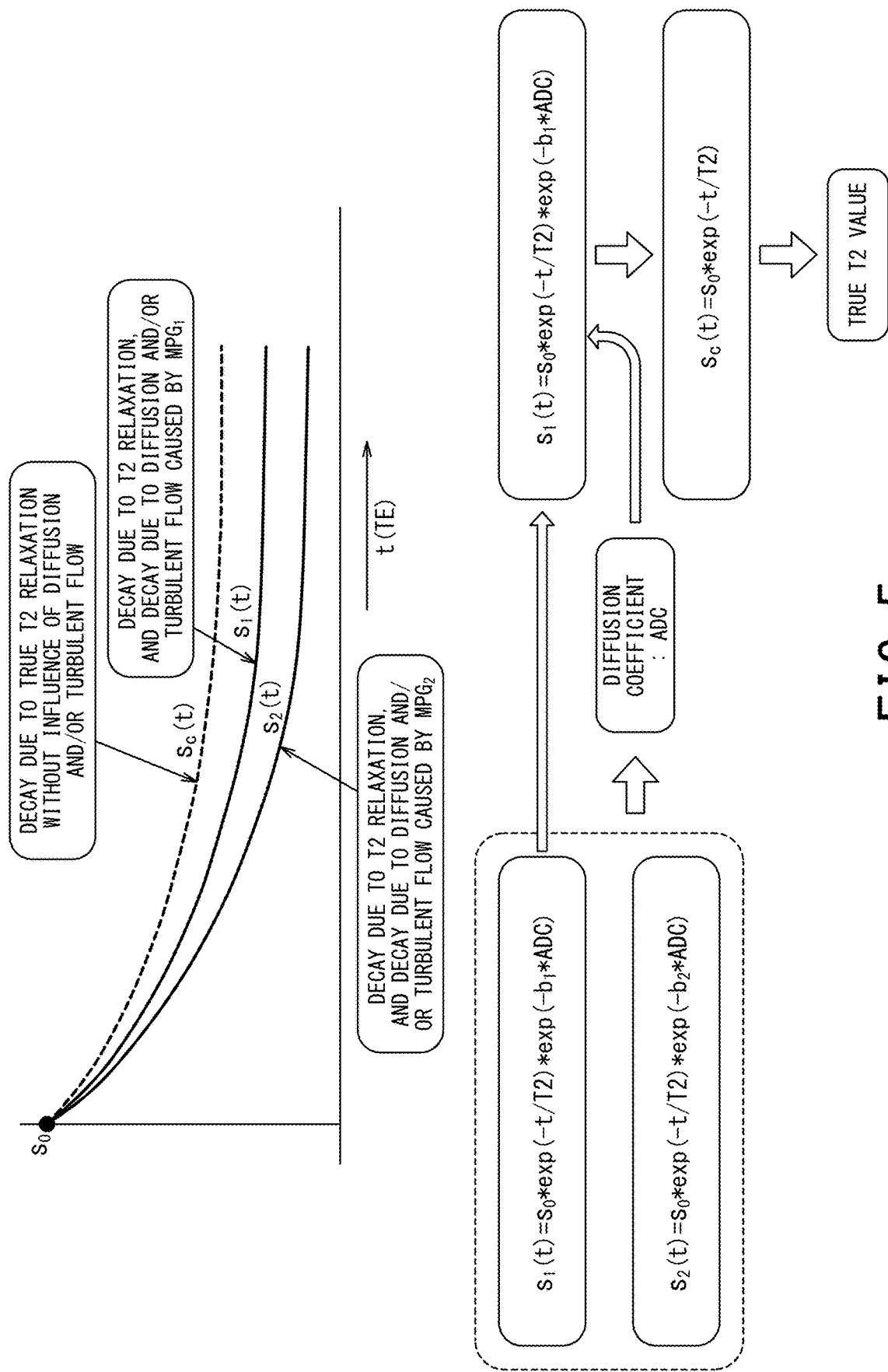
FIG. 5 is a schematic diagram illustrating a processing concept for obtaining a true T2 value that is not influenced by diffusion and/or turbulent flow.

FIG. 5 illustrates the processing concept, in which the MR signal $s_1(t)$ obtained by the first pulse sequence and the MR signal $s_2(t)$ obtained by the second pulse sequence is used to calculate a true T2 value that is not influenced by diffusion and/or turbulent flow.

The solid line in the upper graph of FIG. 5 schematically shows the respective decay curves of the MR signal $s_1(t)$ in the first pulse sequence and the MR signal $s_2(t)$ in the second pulse sequence along with the time elapsed after the application of the excitation pulse. Each curve is an envelope of each peak of the MR signals generated during each interval between refocusing pulses.

As described above, the MR signal $s_1(t)$ in the first pulse sequence is decayed by T2 relaxation and perfusion and/or turbulent flow due to the $MPG_1$ pulse. The MR signal $s_1(t)$ can be represented by, for example, Expression 1 below.

$$s_1(t)=s_0 * \exp(-t/T2) * \exp(-b_1 * ADC) \quad \text{Expression 1}$$

In Expression 1, "t" represents the elapsed time from the application of the excitation pulse, T2 represents the transverse relaxation time value T2 of the imaging target, and ADC represents an apparent diffusion coefficient which is an index of perfusion and/or turbulent flow of the imaging target. In the following, the ADC is simply referred to as the diffusion coefficient. In Expression 1, $b_1$ is an index (b-value) showing the MPG effect by the $MPG_1$ pulse, and a known value that can be calculated from the time waveform of the $MPG_1$ pulse.

Similarly, the MR signal $s_2(t)$ in the second pulse sequence can be represented by, for example, Expression 2 below.

$$s_2(t)=s_0*\exp(-t/T2)*\exp(-b_2*ADC) \quad \text{Expression 2}$$

The only difference between Expression 1 and Expression 2 is $b_2$. In Expression 2, $b_2$ is also an index showing the MPG effect by the $MPG_2$ pulse and a known value that can be calculated from the time waveform of the $MPG_2$ pulse.

Since $b_1$ and $b_2$ are known values, the diffusion coefficient ADC can be calculated from Expression 1 and Expression 2. Further, when the calculated ADC and $b_1$ as the known b-value are substituted into Expression 1, Expression 3 can be obtained as below.

$$s_c(t)=s_0*\exp(-t/T2) \quad \text{Expression 3}$$

Expression 3 represents the corrected MR signal $s_c(t)$. In Expression 3, $\exp(-b_1*ADC)$, which is the decay term of the diffusion coefficient ADC in Expression 1, is removed. Thus, Expression 3 is composed only of the term of $\exp(-t/T2)$, which is the decay term due to T2 decay, and is not influenced by the perfusion and/or turbulent flow of the imaging target. Hence, the true T2 value without the influence of perfusion and/or turbulent flow can be calculated from the decay curve according to Expression 3.

The concept of the first and second pulse sequences shown in FIG. 4A to FIG. 4F and the processing of the present embodiment shown in FIG. 5 are based on the assumption that the same T2 value and the same diffusion coefficient ADC is uniform over the entire imaging target. However, in reality, the T2 value and the diffusion coefficient ADC should show different values depending on the position of the imaging target. Thus, in the present embodiment, the diffusion coefficient ADC is calculated for each pixel position of the reconstructed image, and the true T2 value without influence of perfusion and/or turbulent flow is calculated for each pixel position. In other words, it is preferred to calculate an ADC map in which the diffusion coefficients ADCs are arranged for each pixel position, and to calculate a true T2 map in which the true T2 values are arranged for each pixel position. Hereinafter, the calculation processing of the ADC map and the true T2 map according to the present embodiment will be described on the basis of the flowchart of FIG. 6 by referring to FIG. 7A to FIG. 13C as required.

Figure 6:
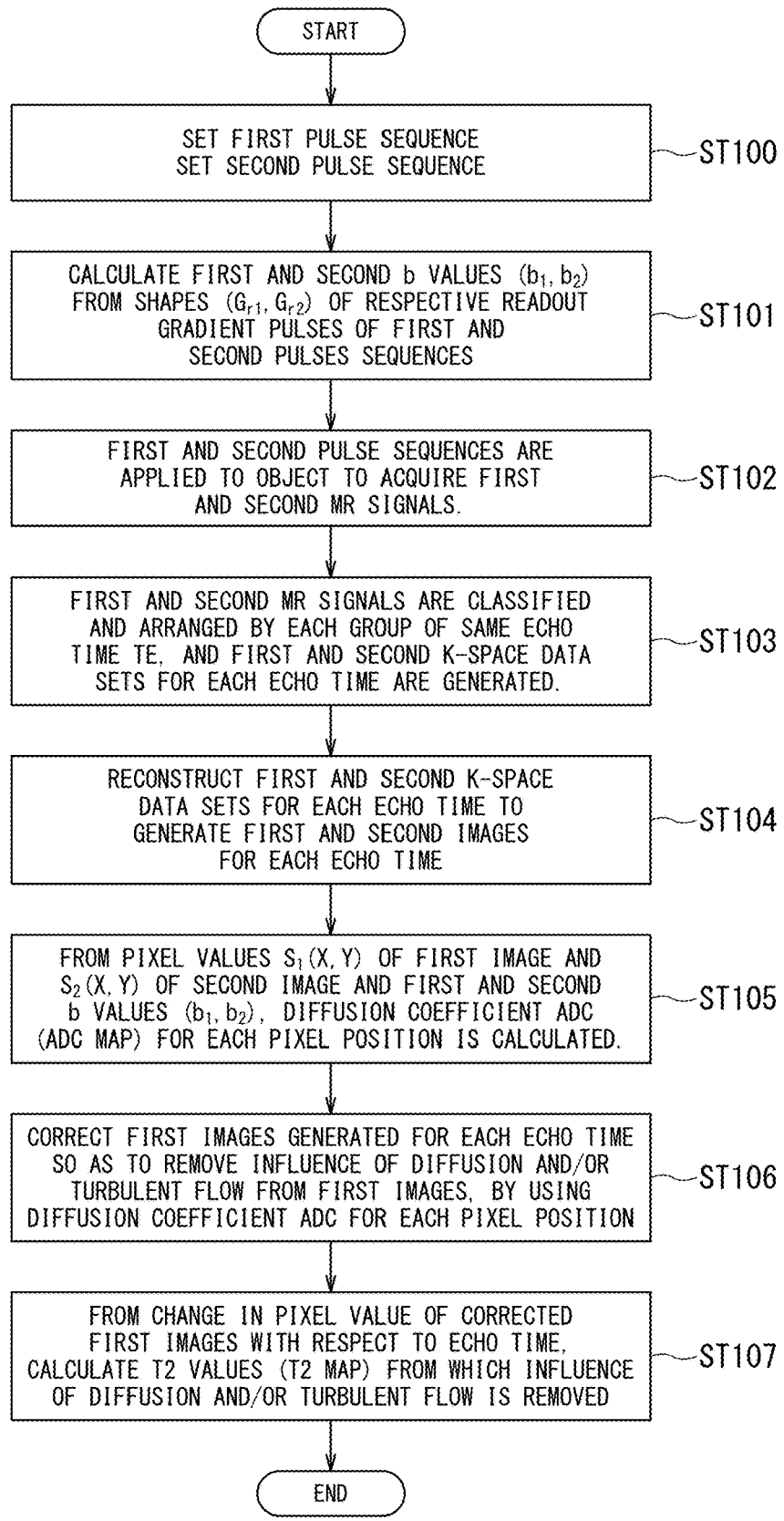
FIG. 6 is a flowchart illustrating processing to be executed by the MRI apparatus of the present embodiment.

First, in the step ST100 in FIG. 6, the first and second pulse sequences are set. The processing of the step ST100 is performed by the imaging-condition setting function F01 in FIG. 3. FIG. 7A to FIG. 9C are diagrams illustrating the first and second pulse sequences set in the step ST100.

FIG. 7A and FIG. 7B are respectively sequence diagrams of the RF pulse and the phase encoding gradient pulse GP that are common to the first and second pulse sequences. FIG. 7C is a sequence diagram of the readout gradient pulse $G_{r_1}$ of the first pulse sequence. FIG. 7D is a sequence diagram of the readout gradient pulse $G_{r_2}$ of the second pulse sequence.

FIG. 8A and FIG. 8B are sequence diagrams of the first and second pulse sequences when viewed over a longer time span than FIG. 7A to FIG. 7D. In FIG. 8B, the solid straight line extending in the horizontal direction corresponds to the phase encode amount of zero, and the value of the phase encode amount is schematically shown by the distance between each black square and the solid straight line.

As shown in FIG. 7B, FIG. 8A, and FIG. 8B, in the first and second pulse sequences, the plurality of refocusing pulses are classified into a plurality of groups that are different in echo time TE from each other, and the phase encode amount associated with each refocusing pulse is set to change in a predetermined pattern for each refocusing pulse within each group.

For example, as shown in FIG. 8A and FIG. 8B, the plurality of refocusing pulses are classified into N groups consisting of the group 1 to the group N, and each group has M refocusing pulses. In the case of FIG. 8A, each group includes five refocusing pulses. The phase encode amount associated with each refocusing pulse is set such that the phase encode amount changes for each refocusing pulse within each group in a predetermined pattern, for example, "+2P, +P, 0, −P, −2p" wherein "P" is a predetermined unit of phase encode amount.

The elapsed time from the application of the excitation pulse to the center of each group is considered to be the echo time TE representing each group. In other words, it is considered that MR signals corresponding to the echo times TE1, TE2, TE3, . . . , TE (N) can be respectively obtained in the group 1, group 2, group 3, . . . , Group N.

Further, as shown in FIG. 8A, the first and second pulse sequences are set such that application of one segment, which is composed of one excitation pulse and the subsequent refocusing pulses, is repeated a predetermined number of times (for example, L times) during a repetition time TR.

The phase encode amount is set such that the change pattern of the phase encode amount in each group is different between different segments. For example, as shown in FIG. 8B, when the change pattern of the phase encode amount of every group in the first segment is "+2P, +P, 0, −P, −2P", the change pattern of the phase encode amount of every group in the second segment is set to be, for example, "+2P+α, +P+α, +a, −P+α, −2P+α", where the phase encode amount in the first segment is uniformly shifted by a in the plus direction.

In this way, by making the change pattern of the phase encode amount in the group corresponding to the same echo time TE difference between segments, all k-spaces in the phase encoding direction required for reconstructing the full images for the respective echo times can be filled with k-space data without overlapping.

FIG. 9A to FIG. 9C are schematic diagrams illustrating a concept of filling k-spaces with k-space data (i.e., MR signals) acquired in a plurality of segments. As shown in FIG. 9C, k-space data of groups corresponding to the same echo time TE (i.e., k-space data of groups having the same group number) are acquired from each segment, and k-spaces provided for each of different echo times TE such as TE1, TE2, TE3, . . . , TE(N) are filled.

In this manner, k-space data are acquired by repeating a segment composed of a plurality of groups with different echo times for a plurality of times, and accordingly, each k-space corresponding to different echo times can be fully filled with k-space data that are sufficient for reconstructing complete images.

Although the change pattern of the phase encode amount is common to all the groups in the same segment in the case shown in FIG. 7A to FIG. 9C, the change pattern of the phase encode amount is not limited to the above-described case. The change pattern of phase encode amount between groups in the same segment may be different. The point is that, when acquiring k-space data over a plurality of segments, it is sufficient that each k-space corresponding to different echo times are eventually fully filled, without overlap, with k-space data enough for reconstructing the complete images.

Returning to FIG. 6, in the step ST100, the above-described first and second pulse sequences are set.

In the next step ST101, the first and second b-values ($b_1$ and $b_2$) are calculated from the shapes of the respective MPG pulses ($MPG_1$ and $MPG_2$) in the readout gradient pulse of the first and second pulse sequences by a known method (see FIG. 11A). The processing of the step ST101 is performed by, for example, the ADC map generation function F03.

In the next step ST102, the first and second pulse sequences determined in the step ST100 are applied to the object to acquire the first MR signals and the second MR signals. The processing of the step ST102 is performed by the scanner 600.

In the next step ST103, as described in relation to FIG. 7A to FIG. 9C, each of k-spaces corresponding to the respective different echo times is filled with the digitized first MR signals having the same echo time to constitute a first k-space dataset for each echo time so as to generate the first images. Similarly, each of k-spaces corresponding to the respective different echo times is filled with the digitized second MR signals having the same echo time to constitute a second k-space dataset for each echo time so as to generate the second images. FIG. 10A illustrates the first k-space dataset generated for each echo time from TE1 to TE(N), and FIG. 10C illustrates the second k-space dataset generated for each echo time from TE1 to TE(N).

In the next step ST104, the first and second images for each echo time are generated by reconstructing the first and second k-space datasets for each echo time. FIG. 10A to FIG. 10D illustrate the processing concept of reconstructing the first and second k-space datasets for each echo time to generate the first and second images for each echo time. The processing of the steps ST103 and ST104 is performed by, for example, the image generation function F02 in FIG. 2.

In the next step ST105, the diffusion coefficient ADC (i.e., ADC map) for each pixel position is calculated from each pixel value $S_1(x, y)$ of the first image, each pixel value $S_2(x, y)$ of the second image, and the first and second b-values (b1, b2). The processing of the step ST105 is performed by the ADC map generation function F03 in FIG. 2.

FIG. 11A to FIG. 11C illustrate the processing concept of the step ST105. As shown in FIG. 11B, the pixel value $S_1(x, y)$ of the first image is subjected to T2 decay $\{\exp(-TE(n)/T2)\}$ depending on the echo time TE(n) and the T2 value of the tissue of the object at the pixel position (x, y), and is also subjected to decay $\{\exp(-b_1*ADC(x, y))\}$, for each readout, by perfusion and/or turbulent flow depending on the diffusion coefficient ADC at the pixel position (x, y) and the $b_1$ value of the first pulse sequence. When M times of readouts are performed between TE(n+1) and TE(n), the pixel value $S_1(x, y)$ of the first image is subjected to decay effectively corresponding to the (M*b1) value as the MPG effect. In the case of FIG. 7, M=5, for example. The effective b-value integrated between two adjacent echo times is used in the following for convenience. In this case, the pixel value $S_1(x, y)$ of the first image can be expressed by Expression 4 below.

$$S_1(x,y)=S_0(x,y)*\exp(-TE(n)/T2)*\exp(-b_1*ADC(x,y)) \quad \text{Expression 4}$$

Similarly, as shown in FIG. 11C, the pixel value $S_2(x, y)$ of the second image is subjected to T2 decay $\{\exp(-TE(n)/T2)\}$ depending on the echo time TE(n) and the T2 value of the tissue of the object at the pixel position (x, y), and is also subjected to decay $\{\exp(-b_2*ADC(x, y))\}$ by perfusion and/or turbulent flow depending on the diffusion coefficient ADC at the pixel position (x, y) and the $b_2$ value of the second pulse sequence. Accordingly, the pixel value $S_2(x, y)$ of the second image can be expressed by Expression 5 below.

$$S_2(x,y)=S_0(x,y)*\exp(-TE(n)/T2)*\exp(-b_2*ADC(x,y)) \quad \text{Expression 5}$$

By calculating the ratio of Expression 4 to Expression 5 as $\{S_1(x, y)/S_2(x, y)\}$, only the decay term due to perfusion and/or turbulent flow remains. Since the b-values ($b_1, b_2$) are known, the diffusion coefficient ADC(x, y) for each pixel position can be calculated. Further, the ADC map as shown in FIG. 11D can be generated by arranging the respective diffusion coefficients ADC(x, y) at the corresponding pixel positions.

In the next step ST106, the diffusion coefficient ADC for each pixel position (i.e., the ADC map) is used to correct the first images generated for each echo time, and the influence of diffusion and/or turbulence is removed from the first images. The processing of the step ST106 is performed by the diffusion/motion correction function F04 in FIG. 2.

FIG. 12A to FIG. 12C are schematic diagrams illustrating the processing concept of the step ST106. FIG. 12A shows the first images for each echo time TE(n) before correction wherein n is 1 to N, and these uncorrected first images are influenced by perfusion and/or turbulent flow. Each pixel value of the first image before correction is subjected to decay by perfusion and/or turbulent flow $\{\exp(-b_1*ADC(x, y))\}$ depending on the $b_1$ value of the first pulse sequence as shown in Expression 4.

This decay then is corrected for each pixel position by using the ADC map (FIG. 12B) calculated in the step ST105. Consequently, as shown in FIG. 12C, the corrected first images (i.e., first images after correction) that are not influenced by the perfusion and/or turbulent flow are calculated for each echo time TE(n) wherein n is 1 to N. Each pixel value $S_c(x, y)$ of each first image after correction is represented by Expression 6 below.

$$S_c(x,y)=S_0(x,y)*\exp(-TE(n)/T2) \quad \text{Expression 6}$$

In the next step ST107, the true T2 value, from which the influence of diffusion and/or turbulence is removed, is calculated for each pixel position based on the change in pixel value of the corrected first image with respect to the echo time TE, and the T2 map is generated by arranging the true T2 values at corresponding pixel positions. The processing of the step ST107 is performed by the T2 map generation function F05 in FIG. 2.

FIG. 13A to FIG. 13C are schematic diagrams illustrating the processing concept of the step ST107. The curve shown by the broken line in FIG. 13B is a schematic graph in which the pixel value $S_c(x, y)$ of the corrected first image is marked with a dot with respect to the echo time TE. The curve shown by the solid line in FIG. 13B is a schematic graph in which the pixel value $S_1(x, y)$ of the first image before correction is marked with a dot with respect to the echo time TE.

Under the assumption that the pixel value $S_c(x, y)$ of the corrected first image changes by an exponential function, the T2 value can be calculated when pixel values $S_c(x, y)$ for at least two echo times TE are available. However, the calculation accuracy of the T2 value can be enhanced by increasing the sample points of the echo time TE and using a method such as curve fitting.

In addition, multi-component substances showing different T2 values in the same pixel position (i.e., in the same voxel) may be included. Even in such a case, the T2 value of each component can be estimated from the change curve of the pixel value $S_c(x, y)$ corresponding to two or more echo times TE.

Then, by arranging the T2 values calculated for each pixel position (i.e., true T2 values that are not influenced by perfusion and/or turbulent flow) at the corresponding pixel positions, the true T2 map can be generated as shown in FIG. 13C.

Figures 14A, 14B:
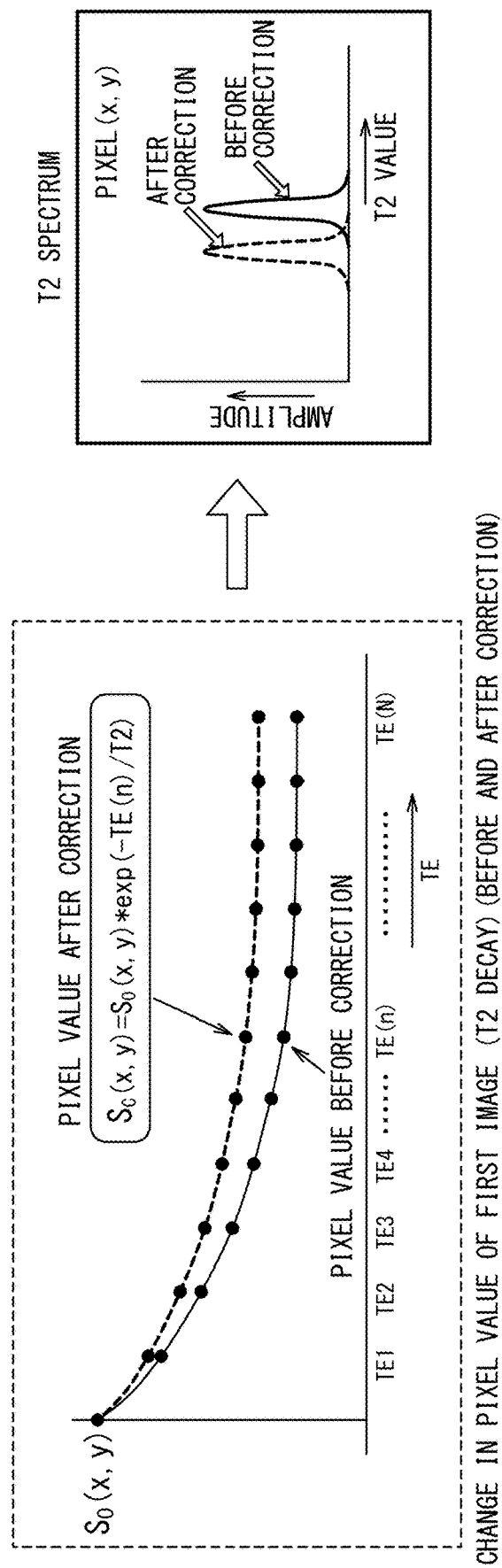
FIG. 14A and FIG. 14B are schematic diagrams illustrating a processing concept of calculating a T2 spectrum from change in pixel value of the first image after correction with respect to the echo time TE.

The T2 spectrum illustrated in FIG. 14B can also be calculated from the change curve (FIG. 14A) of each pixel value $S_c(x, y)$ of the corrected first image with respect to the echo time TE. The T2 spectrum is obtained by marking the horizontal axis showing the T2 value of each pixel and the vertical axis showing the relative amplitude (i.e., normalized pixel value) of each pixel. Under the influence of perfusion and/or turbulent flow, the peak of the T2 spectrum shows a larger T2 value compared with the peak of the true T2 spectrum obtained by correction. On the other hand, in the T2 spectrum based on the true T2 values calculated from the change in pixel value after correction, the spectrum peak appears at the correct position of the T2 value. The calculation processing of the T2 spectrum is performed by the T2 spectrum generation function F06 in FIG. 2.

First Modification

FIG. 15A to FIG. 15C are sequence diagrams of the first and second pulse sequences according to the first modification of the present embodiment. In the first modification, while the first pulse sequence (FIG. 15A and FIG. 15B) is the same as the above-described embodiment, the readout gradient pulse of the second pulse sequences is slightly different from the above-described embodiment as shown in FIG. 15C.

Specifically, in the readout gradient pulse of the second pulse sequence, the same readout gradient pulse as that of the first pulse sequence is applied (i.e., the additional gradient pulse is not added) during the predetermined echo time TEa from the application of the excitation pulse, and the additional gradient pulse is added after the predetermined echo time TEa elapsed.

The main imaging target of the MRI apparatus 1 of the present embodiment is a body fluid such as CSF having a relatively long T2 relaxation time. Thus, as a correction process, it is usually sufficient to target a signal having an echo time TE longer than a predetermined echo time TEa. Since the additional gradient pulse is not added in the period from the application of the excitation pulse to the predetermined echo time TEa, the burden on the MRI apparatus 1 is reduced. Further, by using data acquired by adding the additional gradient pulse to limit the processing, such as the reconstruction of the first and second images, the correction of the first images, calculation of T2 values using the corrected first images, time for such processing can be shortened.

Second Modification

Figure 16A:
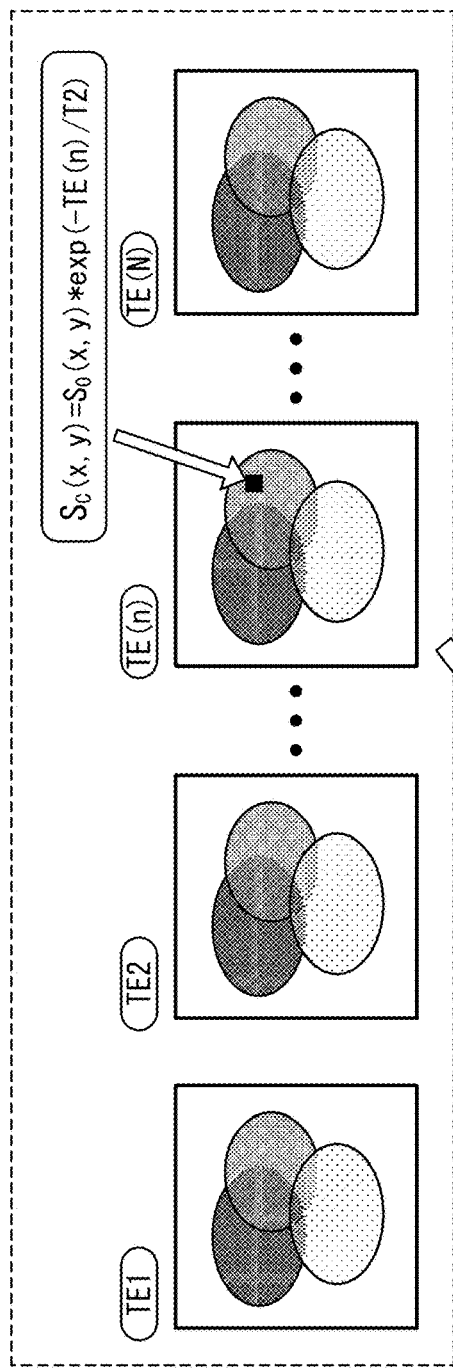
FIG. 16A to FIG. 16C are schematic diagrams illustrating a processing concept of the second modification of the present embodiment.
Figure 16B:
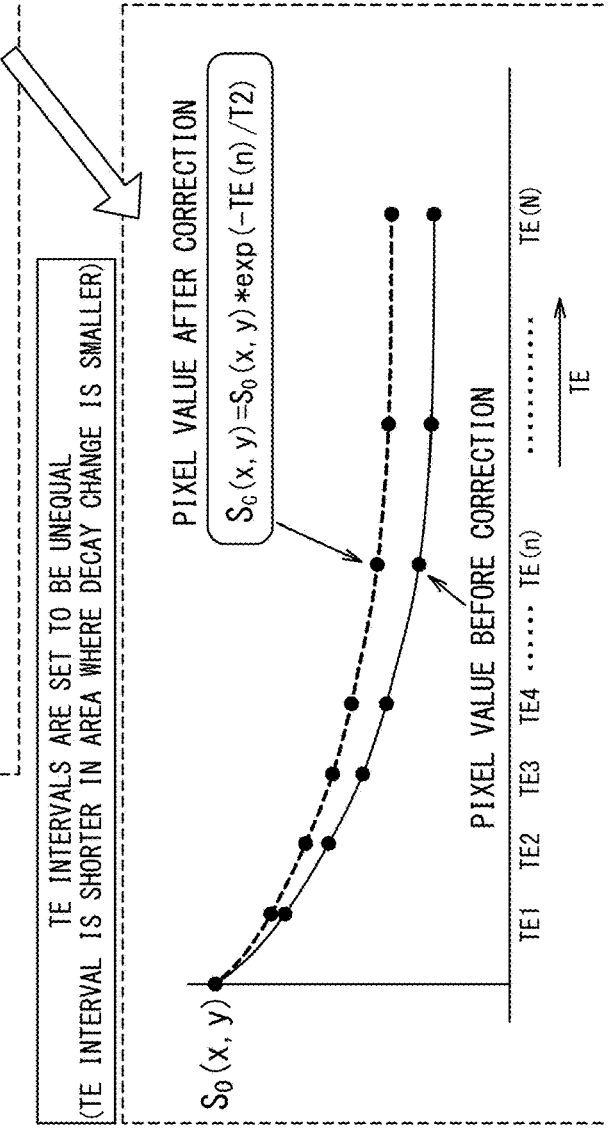
Figure 16C:
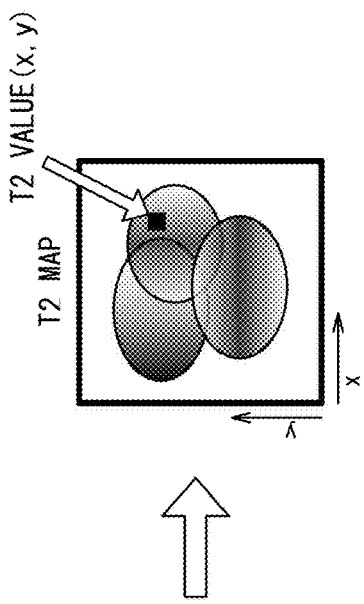

FIG. 16A to FIG. 16C are schematic diagrams illustrating a processing concept of the second modification of the present embodiment. In the second modification as shown in FIG. 16B, unlike FIG. 14, the intervals of the echo times TE are set to be unequal by thinning out some of the first and second images. As described above, the T2 value is calculated from the curve of the pixel values of the corrected first image with respect to the echo time TE. Normally, change of this curve is larger in the region where the echo time TE is short, and becomes smaller as the echo time TE becomes longer. Thus, in the region where the echo time TE is short, data are acquired at equal intervals as shown in FIG. 14A. On the other hand, in the region where the echo time TE is long, the interval between two adjacent echo times is set to be longer than the region where the echo time TE is short. By generating the first images from the data acquired in this manner, the total number of generated images can be reduced without degrading the calculation accuracy of the T2 values, and the processing time required for calculating and analyzing the T2 values can be shortened.

Third Modification

In the above-described embodiments, the application direction of each readout gradient pulse of the second pulse sequence is set to be the same as the application direction of each readout gradient pulse of the first pulse sequence.

In the third modification, the imaging-condition setting function F01 sets a third pulse sequence in which the application direction of the readout gradient pulse is orthogonal to the application direction of the readout gradient pulse of the second pulse sequence. Further, imaging-condition setting function F01 sets a fourth pulse sequence in which the application direction of the readout gradient pulse is orthogonal to both of the application direction of the readout gradient pulse of the second pulse sequence and the application direction of the readout gradient pulse of the third pulse sequence.

Similar to the readout gradient pulse in the second pulse sequence, each readout gradient pulse in the third and fourth pulse sequences is a pulse in which two additional gradient pulse are added to the respective front and trailing edges of the readout gradient pulse in the first pulse sequence, and has a predetermined magnitude of the MPG effect.

Based on the respective MR signals acquired by applying the above-described second to fourth (i.e., second, third, and fourth) pulse sequences to the object, the image generation function F02 according to the third modification generates at least one of: a set of respective diffusion-weighted images based on the second to fourth pulse sequences; a set of respective diffusion coefficient images based on the second to fourth pulse sequences; and a diffusion tensor image.

As described above, the MRI apparatus of each embodiment can acquire a highly accurate T2 value and an index related to diffusion and/or turbulent flow in a short imaging time.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:
1. An MRI apparatus, comprising:
a scanner that includes a static magnetic field magnet, a gradient coil, a whole body coil, and an RF transmitter; and
processing circuitry configured to:
set a first pulse sequence and a second pulse sequence, each of which is a fast spin echo (FSE) pulse sequence in which a plurality of refocusing pulses are applied subsequent to an application of an excitation pulse,
wherein, in the first pulse sequence, a first gradient pulse that produces a motion probing gradient effect is applied along a readout direction between each of a plurality of refocusing pulses, and, in the second pulse sequence, a second gradient pulse being that produces the motion probing gradient effect and is different in pulse shape from the first gradient pulse is applied along the readout direction between each of the plurality of refocusing pulses, wherein:
the scanner is configured to apply the first pulse sequence and the second pulse sequence to an object and acquire a plurality of first signals in the first pulse sequence and a plurality of second signals in the second pulse sequence, wherein the plurality of first signals have the motion probing gradient effect depending on the first pulse sequence and the plurality of second signals have the motion probing gradient effect depending on the second pulse sequence; and
the processing circuitry is further configured to
generate a plurality of first images from the plurality of first signals and a plurality of second images from the plurality of second signals, wherein the plurality of first images have different echo times from each other and the plurality of second images have different echo times from each other; and
calculate a T2 value of a body fluid of the object from the plurality of first images and the plurality of second images in a manner that an influence of diffusion of the body fluid is removed from the T2 value by using an index related to diffusion of the body fluid.

2. The MRI apparatus according to claim 1, wherein the processing circuitry is further configured to set the first gradient pulse and the second gradient pulse in such a manner that a time integral value of the second gradient pulse in the second pulse sequence is larger than a time integral value of the first gradient pulse in the first pulse sequence.

3. The MRI apparatus according to claim 1, wherein the processing circuitry is further configured to calculate the index related to the diffusion of the body fluid.

4. The MRI apparatus according to claim 1, wherein the second gradient pulse set by the processing circuitry is configured by adding an additional gradient pulse having a predetermined shape to each of a front edge side and a trailing edge side of the first gradient pulse.

5. The MRI apparatus according to claim 1, wherein, in each of the first pulse sequence and the second pulse sequence, the plurality of refocusing pulses are classified into a plurality of groups being different in echo time from each other, and the processing circuitry is further configured to set a phase encode amount associated with each refocusing pulse in a manner that the phase encode amount changes in a predetermined change pattern for each refocusing pulse in each group.

6. The MRI apparatus according to claim 5, wherein the processing circuitry is further configured to set the predetermined change pattern of the phase encode amount to be different between the plurality of groups.

7. The MRI apparatus according to claim 5, wherein the processing circuitry is further configured to set the predetermined change pattern of the phase encode amount in a manner that a same change pattern is repeated in each group.

8. The MRI apparatus according to claim 5, wherein the processing circuitry is further configured to:
set each of the first pulse sequence and the second pulse sequence to be repeated by a predetermined number of repetition times; and
both among the repeated first pulse sequences and among the repeated second pulse sequences, set the phase encode amount in each of the groups corresponding to the same echo time so as not to overlap with each other and to fill k-space required for reconstructing a complete image.

9. The MRI apparatus according to claim 1, wherein the processing circuitry is further configured to:
calculate a first b-value from an amplitude and a shape of the first gradient pulse;
calculate a second b-value from an amplitude and a shape of the second gradient pulse; and
calculate an ADC map from pixel values of the plurality of first images generated from the plurality of first signals, pixel values of the plurality of second images generated from the plurality of second signals, the first b-value, and the second b-value, wherein, in the ADC map, values of the index related to movement including diffusion of the body fluid of the object are arranged for each pixel position.

10. The MRI apparatus according to claim 9, wherein the processing circuitry is further configured to correct each pixel value of the plurality of first images by using the values of the index in the ADC map in a manner that the T2 value of the body fluid without the influence of the diffusion of the body fluid is reflected in the plurality of first images.

11. The MRI apparatus according to claim 10, wherein the processing circuitry is further configured to:
correct each pixel value of each of the plurality of first images by using the index in the ADC map; and
correct the plurality of first images in such a manner that the T2 value of the body fluid without the influence of the diffusion of the body fluid is reflected in the plurality of first images.

12. The MRI apparatus according to claim 11, wherein the processing circuitry is further configured to generate a T2 map by calculating the T2 value for each pixel from a change in pixel value at a same pixel position between the plurality of the first images after correction.

13. The MRI apparatus according to claim 11, wherein the processing circuitry is further configured to calculate a T2 spectrum for each pixel from a change in pixel value at a same pixel position between the plurality of first images after correction.

14. The MRI apparatus according to claim 1, wherein the processing circuitry is further configured to:
set a third pulse sequence having a third gradient pulse and a fourth pulse sequence having a fourth gradient pulse in a manner that (i) an application direction of the third gradient pulse is orthogonal to the application direction of the second gradient pulse, and (ii) an application direction of the fourth gradient pulse is orthogonal to both of the application direction of the second gradient pulse and the application direction of the third gradient pulse; and
generate at least one of (i) a set of respective diffusion-weighted images based on the second, third, and fourth pulse sequences, (ii) a set of respective diffusion coefficient image based on the second, third, and fourth pulse sequences, and (iii) a diffusion tensor image, by using respective signals acquired by applying the second, third, and fourth pulse sequences to the object.

15. The MRI apparatus according to claim 4, wherein the processing circuitry is further configured to apply the additional gradient pulse in the second pulse sequence at each interval between the refocusing pulses that are applied after elapse of a predetermined echo time from application of the excitation pulse.

16. The MRI apparatus according to claim 1, wherein the processing circuitry is further configured to:
set unequal intervals of the echo time by only generating a reduced number of first images and a reduced number of second images, wherein the reduced number of first images is less than a number of the refocusing pulses of the first pulse sequence and the reduced number of second images is less than a number of the refocusing pulses of the second pulse sequence; and
calculate the T2 value by using the reduced number of the first images and the reduced number of the second images.

17. The MRI apparatus according to claim 1, wherein:
the body fluid of the object is at least one of cerebrospinal fluid and cerebral interstitial fluid.

18. The MRI apparatus according to claim 1, wherein:
the FSE sequence is a Carr-Purcell-Meiboom-Gill (CPMG) sequence.

* * * * *